US012797309B2

(12) United States Patent
Braganza et al.

(10) Patent No.: US 12,797,309 B2
(45) Date of Patent: Nov. 17, 2026

(54) PRODUCT COMPOSITION COMPRISING A DISCRETE PARTICLE AND A NON-AQUEOUS BASE

(71) Applicant: The Procter & Gamble Company, Cincinnati, OH (US)

(72) Inventors: Gemma Zoe Braganza, Singapore (SG); Shikhar Gupta, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 222 days.

(21) Appl. No.: 18/757,690

(22) Filed: Jun. 28, 2024

(65) Prior Publication Data

US 2025/0009612 A1 Jan. 9, 2025

Related U.S. Application Data

(60) Provisional application No. 63/510,999, filed on Jun. 29, 2023.

(51) Int. Cl.
*A61K 8/04* (2006.01)
*A61Q 5/12* (2006.01)

(52) U.S. Cl.
CPC .................. *A61K 8/04* (2013.01); *A61Q 5/12* (2013.01); *A61K 2800/31* (2013.01); *A61K 2800/33* (2013.01)

(58) Field of Classification Search
None
See application file for complete search history.

(56) References Cited

U.S. PATENT DOCUMENTS

| | | | |
|---|---|---|---|
| 1,108,367 | A | 8/1914 | Holtermann |
| 1,489,388 | A | 4/1924 | Glenn |
| 1,600,340 | A | 9/1926 | Kobbe |
| 1,612,255 | A | 12/1926 | Borreca |
| 2,438,091 | A | 3/1948 | Lynch |
| 2,528,378 | A | 10/1950 | Mannheimer |
| 2,658,072 | A | 11/1953 | Kosmin |
| 2,809,971 | A | 10/1957 | Bernstein et al. |
| 2,879,231 | A | 3/1959 | Marshall |
| 3,219,656 | A | 11/1965 | Boettner |
| 3,236,733 | A | 2/1966 | Karsten et al. |
| 3,373,208 | A | 3/1968 | Blumenthal |
| 3,636,113 | A | 1/1972 | Hall |
| 3,709,437 | A | 1/1973 | Wright |
| 3,716,498 | A | 2/1973 | Hall |
| 3,753,196 | A | 8/1973 | Kurtz et al. |
| 3,761,418 | A | 9/1973 | Parran |
| 3,792,068 | A | 2/1974 | Luedders et al. |
| 3,887,692 | A | 6/1975 | Gilman |
| 3,904,741 | A | 9/1975 | Jones et al. |
| 3,950,532 | A | 4/1976 | Bouillon et al. |
| 3,958,581 | A | 5/1976 | Abegg et al. |
| 3,959,160 | A | 5/1976 | Horsler et al. |
| 3,962,418 | A | 6/1976 | Birkofer |
| 4,049,792 | A | 9/1977 | Elsnau |
| 4,089,945 | A | 5/1978 | Brinkman et al. |
| 4,120,948 | A | 10/1978 | Shelton |
| 4,137,180 | A | 1/1979 | Naik |
| 4,237,155 | A | 12/1980 | Kardouche |
| 4,275,055 | A | 6/1981 | Nachtigal et al. |
| 4,309,119 | A | 1/1982 | Wittersheim |
| 4,323,683 | A | 4/1982 | Bolich, Jr. et al. |
| 4,329,334 | A | 5/1982 | Su et al. |
| 4,345,080 | A | 8/1982 | Bolich, Jr. |
| 4,359,456 | A | 11/1982 | Gosling et al. |
| 4,379,753 | A | 4/1983 | Bolich, Jr. |
| 4,430,243 | A | 2/1984 | Bragg |
| 4,470,982 | A | 9/1984 | Winkler |
| 4,726,945 | A | 2/1988 | Patel |
| 4,732,696 | A | 3/1988 | Urfer |
| 4,795,327 | A | 1/1989 | Gaylord |
| 4,839,166 | A | 6/1989 | Grollier et al. |
| 4,854,333 | A | 8/1989 | Inman et al. |
| 4,867,971 | A | 9/1989 | Ryan et al. |
| 4,891,214 | A | 1/1990 | Stevens |
| 4,931,274 | A | 6/1990 | Barabino et al. |
| 4,973,416 | A | 11/1990 | Kennedy |
| 4,985,238 | A | 1/1991 | Tanner et al. |
| 4,997,641 | A | 3/1991 | Hartnett |
| 5,019,375 | A | 5/1991 | Tanner et al. |
| 5,093,112 | A | 3/1992 | Birtwistle et al. |

(Continued)

FOREIGN PATENT DOCUMENTS

| | | | |
|---|---|---|---|
| BE | 825146 | A | 8/1975 |
| BR | 199400875 | A | 10/1995 |

(Continued)

OTHER PUBLICATIONS

"Anti-Dandruff Shampoo", Mintel Database, Record No. 752198, dated Aug. 2007 ; pp. 1-3.
"Cleansing Pack" Mintel Database, Retrieved from the Internet: https://www.gnpd.com, Apr. 6, 2018, 3 Pages.
"Comparative Study on the Chemical constituents of Aloe Vera and Aloe Kula in China", Zhang Xiaohua et al., Flavor Cosmetics, No. 63, dated Dec. 31, 2000, pp. 7-11.
"Conditioner Soap Bar" Mintel Database, Retrieved from the Internet: https://www.gnpd.com, Feb. 15, 2018, 4 Pages.
"Dandruff Control Shampoo", Mintel Database, Record No. 2300131, dated Jan. 2014; pp. 1-2.
"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.

(Continued)

*Primary Examiner* — Ali Soroush
*Assistant Examiner* — Afua Bamfoaa Boateng
(74) *Attorney, Agent, or Firm* — Abbey A. Lopez; John G. Powell

(57) ABSTRACT

A personal care composition that contains discrete particles of a mixture composition and a non-aqueous, fluid base composition. The mixture composition is made from a surfactant, a high melting point fatty compound, and other optional ingredients. The non-aqueous base is at least 75% of a fluid that is not a hydrogen donor.

18 Claims, 1 Drawing Sheet

(56) References Cited

U.S. PATENT DOCUMENTS

| | | | |
|---|---|---|---|
| 5,104,646 | A | 4/1992 | Bolich, Jr. |
| 5,106,609 | A | 4/1992 | Bolich, Jr. |
| 5,135,747 | A | 8/1992 | Faryniarz et al. |
| 5,156,834 | A | 10/1992 | Beckmeyer et al. |
| 5,294,644 | A | 3/1994 | Login et al. |
| 5,296,157 | A | 3/1994 | Macgilp et al. |
| 5,296,622 | A | 3/1994 | Uphues |
| 5,298,640 | A | 3/1994 | Callaghan et al. |
| 5,332,569 | A | 7/1994 | Wood et al. |
| 5,364,031 | A | 11/1994 | Taniguchi et al. |
| 5,374,421 | A | 12/1994 | Tashiro |
| 5,374,614 | A | 12/1994 | Behan et al. |
| 5,409,695 | A | 4/1995 | Abrutyn et al. |
| 5,415,810 | A | 5/1995 | Lee et al. |
| 5,417,965 | A | 5/1995 | Janchitraponvej et al. |
| 5,429,816 | A | 7/1995 | Hofrichter et al. |
| 5,439,682 | A | 8/1995 | Wivell |
| 5,441,659 | A | 8/1995 | Minor |
| 5,486,303 | A | 1/1996 | Capeci |
| 5,489,392 | A | 2/1996 | Capeci |
| 5,496,488 | A | 3/1996 | Kacher et al. |
| 5,516,448 | A | 5/1996 | Capeci |
| 5,536,493 | A | 7/1996 | Dubief |
| 5,554,588 | A | 9/1996 | Behan et al. |
| 5,560,918 | A | 10/1996 | Wivell |
| 5,565,422 | A | 10/1996 | Del |
| 5,569,645 | A | 10/1996 | Dinniwell |
| 5,574,005 | A | 11/1996 | Welch |
| 5,576,282 | A | 11/1996 | Miracle |
| 5,578,298 | A | 11/1996 | Berthiaume |
| 5,595,967 | A | 1/1997 | Miracle |
| 5,597,936 | A | 1/1997 | Perkins |
| 5,599,549 | A | 2/1997 | Wivell |
| 5,624,666 | A | 4/1997 | Coffindaffer et al. |
| 5,635,469 | A | 6/1997 | Fowler et al. |
| 5,665,267 | A | 9/1997 | Dowell et al. |
| 5,691,297 | A | 11/1997 | Nassano |
| 5,714,137 | A | 2/1998 | Trinh |
| 5,747,436 | A | 5/1998 | Patel |
| 5,776,444 | A | 7/1998 | Birtwistle et al. |
| 5,800,897 | A | 9/1998 | Sharma |
| 5,816,446 | A | 10/1998 | Steindorf et al. |
| 5,830,440 | A | 11/1998 | Sturla et al. |
| 5,853,618 | A | 12/1998 | Barker |
| 5,876,705 | A | 3/1999 | Uchiyama et al. |
| 5,879,584 | A | 3/1999 | Bianchetti |
| 5,891,424 | A | 4/1999 | Bretzler et al. |
| 5,902,225 | A | 5/1999 | Monson |
| 5,925,603 | A | 7/1999 | D'Angelo |
| 5,942,217 | A | 8/1999 | Woo et al. |
| 5,955,066 | A | 9/1999 | Sako et al. |
| 5,976,514 | A | 11/1999 | Guskey et al. |
| 5,980,877 | A | 11/1999 | Baravetto |
| 5,985,255 | A | 11/1999 | Vanlerberghe et al. |
| 5,985,939 | A | 11/1999 | Minor |
| 6,015,547 | A | 1/2000 | Yam |
| 6,015,780 | A | 1/2000 | Llosas Bigorra et al. |
| 6,020,303 | A | 2/2000 | Cripe et al. |
| 6,039,933 | A | 3/2000 | Samain et al. |
| 6,046,152 | A | 4/2000 | Vinson et al. |
| 6,060,443 | A | 5/2000 | Cripe et al. |
| 6,087,309 | A | 7/2000 | Vinson et al. |
| 6,110,451 | A | 8/2000 | Matz et al. |
| 6,133,222 | A | 10/2000 | Vinson et al. |
| 6,139,828 | A | 10/2000 | Mccullough |
| 6,153,567 | A | 11/2000 | Hughes |
| 6,153,569 | A | 11/2000 | Halloran |
| 6,162,834 | A | 12/2000 | Sebillotte-Arnaud et al. |
| 6,180,121 | B1 | 1/2001 | Guenin et al. |
| 6,225,464 | B1 | 5/2001 | Hiler, II |
| 6,231,844 | B1 | 5/2001 | Nambu |
| 6,232,302 | B1 | 5/2001 | Alberico et al. |
| 6,248,135 | B1 | 6/2001 | Trinh et al. |
| 6,268,431 | B1 | 7/2001 | Snyder et al. |
| 6,284,225 | B1 | 9/2001 | Bhatt |
| 6,297,203 | B1 | 10/2001 | Guskey |
| 6,329,331 | B1 | 12/2001 | Aronson |
| 6,335,312 | B1 | 1/2002 | Coffindaffer et al. |
| 6,352,688 | B1 | 3/2002 | Scavone et al. |
| 6,386,392 | B1 | 5/2002 | Argentieri |
| 6,413,920 | B1 | 7/2002 | Bettiol |
| 6,423,305 | B1 | 7/2002 | Cauwet-Martin et al. |
| 6,426,326 | B1 | 7/2002 | Mitra et al. |
| 6,436,442 | B1 | 8/2002 | Woo et al. |
| 6,451,300 | B1 | 9/2002 | Dunlop et al. |
| 6,488,943 | B1 | 12/2002 | Beerse et al. |
| 6,511,669 | B1 | 1/2003 | Garnier et al. |
| 6,565,863 | B1 | 5/2003 | Guillou et al. |
| 6,576,602 | B1 | 6/2003 | Smerznak |
| 6,579,907 | B1 | 6/2003 | Sebillotte-Arnaud et al. |
| 6,627,585 | B1 | 9/2003 | Steer |
| 6,642,194 | B2 | 11/2003 | Harrison |
| 6,649,155 | B1 | 11/2003 | Dunlop et al. |
| 6,656,923 | B1 | 12/2003 | Trinh |
| 6,660,288 | B1 | 12/2003 | Behan et al. |
| 6,679,324 | B2 | 1/2004 | Den et al. |
| 6,716,455 | B2 | 4/2004 | Birkel |
| 6,716,805 | B1 | 4/2004 | Sherry |
| 6,719,967 | B1 | 4/2004 | Brown et al. |
| 6,740,713 | B1 | 5/2004 | Busch et al. |
| 6,743,760 | B1 | 6/2004 | Hardy et al. |
| 6,764,986 | B1 | 7/2004 | Busch et al. |
| 6,767,507 | B1 | 7/2004 | Woo et al. |
| 6,794,356 | B2 | 9/2004 | Turner |
| 6,814,088 | B2 | 11/2004 | Barnabas et al. |
| 6,827,795 | B1 | 12/2004 | Kasturi et al. |
| 6,869,923 | B1 | 3/2005 | Cunningham |
| 6,878,368 | B2 | 4/2005 | Ohta et al. |
| 6,897,253 | B2 | 5/2005 | Schmucker-castner |
| 6,900,170 | B2 | 5/2005 | Instone |
| 6,908,889 | B2 | 6/2005 | Niemiec et al. |
| 6,930,078 | B2 | 8/2005 | Wells |
| 6,992,054 | B2 | 1/2006 | Lee et al. |
| 7,018,978 | B2 | 3/2006 | Miracle et al. |
| 7,030,068 | B2 | 4/2006 | Clare et al. |
| 7,100,767 | B2 | 9/2006 | Chomik et al. |
| 7,151,079 | B2 | 12/2006 | Fack et al. |
| 7,172,099 | B2 | 2/2007 | Hoefte |
| 7,202,198 | B2 | 4/2007 | Gordon et al. |
| 7,217,752 | B2 | 5/2007 | Schmucker-Castner et al. |
| 7,220,408 | B2 | 5/2007 | Decoster et al. |
| 7,223,361 | B2 | 5/2007 | Kvietok |
| 7,223,385 | B2 | 5/2007 | Gawtrey et al. |
| 7,485,289 | B2 | 2/2009 | Gawtrey et al. |
| 7,504,094 | B2 | 3/2009 | Decoster et al. |
| 7,531,497 | B2 | 5/2009 | Midha et al. |
| 7,541,320 | B2 | 6/2009 | Dabkowski et al. |
| 7,598,213 | B2 | 10/2009 | Geary et al. |
| 7,659,233 | B2 | 2/2010 | Hurley et al. |
| 7,666,825 | B2 | 2/2010 | Wagner et al. |
| 7,759,378 | B2 | 7/2010 | Philippe |
| 7,820,609 | B2 | 10/2010 | Soffin et al. |
| 7,829,514 | B2 | 11/2010 | Paul et al. |
| 7,841,036 | B2 | 11/2010 | Smith |
| 7,867,505 | B2 | 1/2011 | Elliott et al. |
| 7,928,053 | B2 | 4/2011 | Hecht et al. |
| 7,977,288 | B2 | 7/2011 | SenGupta |
| 8,007,545 | B2 | 8/2011 | Fujii et al. |
| 8,017,108 | B2 | 9/2011 | Baker |
| 8,058,500 | B2 | 11/2011 | Sojka et al. |
| 8,084,407 | B2 | 12/2011 | Soffin et al. |
| 8,088,721 | B2 | 1/2012 | Soffin et al. |
| 8,119,168 | B2 | 2/2012 | Johnson |
| 8,124,063 | B2 | 2/2012 | Harichian et al. |
| 8,158,571 | B2 | 4/2012 | Alonso |
| 8,300,949 | B2 | 10/2012 | Xu |
| 8,322,631 | B2 | 12/2012 | Richardson et al. |
| 8,343,469 | B2 | 1/2013 | Bierganns et al. |
| 8,349,300 | B2 | 1/2013 | Wells |
| 8,349,301 | B2 | 1/2013 | Wells et al. |
| 8,349,302 | B2 | 1/2013 | Johnson et al. |
| 8,357,359 | B2 | 1/2013 | Woo et al. |
| 8,361,448 | B2 | 1/2013 | Johnson et al. |
| 8,361,449 | B2 | 1/2013 | Wells et al. |

(56) References Cited

U.S. PATENT DOCUMENTS 8,361,450 B2 1/2013 Johnson et al.
8,367,048 B2 2/2013 Wells et al.
8,388,699 B2 3/2013 Wood
8,401,304 B2 3/2013 Cavallaro et al.
8,435,501 B2 5/2013 Peffly et al.
8,437,556 B1 5/2013 Saisan
8,470,305 B2 6/2013 Johnson et al.
8,491,877 B2 7/2013 Schwartz et al.
8,539,631 B2 9/2013 Catalfamo et al.
8,574,561 B1 11/2013 Patel et al.
8,580,725 B2 11/2013 Kuhlman et al.
8,609,600 B2 12/2013 Warr et al.
8,628,760 B2 1/2014 Carter et al.
8,629,095 B2 1/2014 Deleersnyder
8,653,014 B2 2/2014 Hilvert
8,675,919 B2 3/2014 Maladen
8,679,316 B2 3/2014 Brunner et al.
8,680,035 B2 3/2014 Kuhlman et al.
8,699,751 B2 4/2014 Maladen
8,709,337 B2 4/2014 Gruenbacher et al.
8,709,385 B2 4/2014 Tamarkin
8,741,275 B2 6/2014 Dente et al.
8,741,363 B2 6/2014 Albrecht et al.
8,771,765 B1 7/2014 Fernandez
8,772,354 B2 7/2014 Williams et al.
8,795,635 B2 8/2014 Tamarkin et al.
8,877,316 B2 11/2014 Hasenoehrl et al.
8,883,698 B2 11/2014 Scheibel et al.
8,931,711 B2 1/2015 Gruenbacher
8,980,239 B2 3/2015 Staudigel et al.
8,987,187 B2 3/2015 Smets et al.
9,006,162 B1 4/2015 Rizk
9,186,642 B2 11/2015 Dihora et al.
9,187,407 B2 11/2015 Koshti et al.
9,265,727 B1 2/2016 Lowenborg
9,271,908 B2 3/2016 Allef
9,272,164 B2 3/2016 Johnson et al.
9,296,550 B2 3/2016 Smith
9,308,398 B2 4/2016 Hutton et al.
9,393,447 B2 7/2016 Zasloff
9,428,616 B2 8/2016 Wagner
9,511,007 B2 12/2016 Frantz et al.
9,512,275 B2 12/2016 Wagner
9,539,444 B2 1/2017 Kinoshita et al.
9,549,885 B2 1/2017 Aistrup
9,610,239 B2 4/2017 Feng
9,655,821 B2 5/2017 Carter et al.
9,662,291 B2 5/2017 Johnson et al.
9,682,021 B2 6/2017 Tamarkin et al.
9,718,201 B2 8/2017 Swenson
9,776,787 B2 10/2017 Nakajima
9,949,901 B2 4/2018 Zhao et al.
9,949,911 B2 4/2018 Cetti
9,968,535 B2 5/2018 Kitko
9,968,537 B2 5/2018 Sharma
9,993,419 B2 6/2018 Glenn, Jr.
9,993,420 B2 6/2018 Glenn, Jr. et al.
10,039,706 B2 8/2018 Meralli et al.
10,039,939 B2 8/2018 Xavier et al.
10,092,492 B2 10/2018 Terrisse
10,111,815 B2 10/2018 Marsh et al.
10,113,140 B2 10/2018 Frankenbach
10,182,976 B2 1/2019 Staudigel
10,238,685 B2 3/2019 Dunn et al.
10,265,261 B2 4/2019 Park et al.
10,311,575 B2 6/2019 Stofel
10,392,625 B2 8/2019 Jin et al.
10,426,713 B2 10/2019 Song
10,441,519 B2 10/2019 Zhao
10,463,596 B1 11/2019 Custer
10,552,557 B2 2/2020 Frankenbach et al.
10,610,473 B2 4/2020 Hertenstein et al.
10,653,590 B2 5/2020 Torres Rivera
10,751,272 B2 * 8/2020 Yokogi .................... A61K 8/60
10,799,434 B2 10/2020 Torres Rivera
10,842,720 B2 11/2020 Thompson
10,881,597 B2 1/2021 Lane et al.
10,888,505 B2 1/2021 Johnson
10,912,730 B2 2/2021 Fevola
10,912,732 B2 2/2021 Gillis
11,058,620 B2 7/2021 Yokogi
11,116,703 B2 9/2021 Song et al.
11,116,704 B2 9/2021 Song et al.
11,129,775 B2 9/2021 Song et al.
11,129,786 B2 9/2021 Adamy
11,186,636 B2 11/2021 Foltz
11,197,809 B2 12/2021 Hertenstein et al.
11,197,810 B2 12/2021 Hertenstein et al.
11,253,450 B2 2/2022 Lane
11,334,694 B2 5/2022 Cetti et al.
11,334,695 B2 5/2022 Cetti et al.
11,679,065 B2 6/2023 Johnson et al.
11,865,198 B2 1/2024 Kroger Lyons
11,904,036 B2 2/2024 Song
2001/0000467 A1 4/2001 Murray
2001/0006088 A1 7/2001 Lyle
2001/0006621 A1 7/2001 Coupe et al.
2001/0016565 A1 8/2001 Bodet et al.
2002/0012646 A1 1/2002 Royce et al.
2002/0028182 A1 3/2002 Dawson
2002/0037299 A1 3/2002 Turowski-Wanke et al.
2002/0172648 A1 11/2002 Hehner et al.
2002/0193265 A1 12/2002 Perron et al.
2002/0197213 A1 12/2002 Schmenger et al.
2003/0003070 A1 1/2003 Eggers et al.
2003/0008787 A1 1/2003 Mcgee et al.
2003/0008790 A1 1/2003 Carew
2003/0022799 A1 1/2003 Alvarado et al.
2003/0049292 A1 3/2003 Turowski-Wanke et al.
2003/0050150 A1 3/2003 Tanaka
2003/0059377 A1 3/2003 Riley
2003/0083210 A1 5/2003 Goldberg
2003/0103923 A1 6/2003 Ohta
2003/0108501 A1 6/2003 Hofrichter
2003/0113354 A1 6/2003 Schmid
2003/0147842 A1 8/2003 Restle et al.
2003/0154561 A1 8/2003 Patel
2003/0161802 A1 8/2003 Flammer
2003/0180238 A1 9/2003 Sakurai et al.
2003/0180246 A1 9/2003 Frantz et al.
2003/0185867 A1 10/2003 Kerschner et al.
2003/0192922 A1 10/2003 Ceppaluni et al.
2003/0199403 A1 10/2003 Wells
2003/0202952 A1 10/2003 Wells et al.
2003/0223951 A1 12/2003 Geary et al.
2003/0223952 A1 12/2003 Wells et al.
2003/0228272 A1 12/2003 Amjad et al.
2004/0014879 A1 1/2004 Denzer et al.
2004/0064117 A1 4/2004 Hammons
2004/0131660 A1 7/2004 Lange et al.
2004/0136942 A1 7/2004 Yamazaki
2004/0144863 A1 7/2004 Kendrick
2004/0151793 A1 8/2004 Paspaleeva-kuhn et al.
2004/0157754 A1 8/2004 Geary et al.
2004/0229963 A1 11/2004 Stephane
2004/0234484 A1 11/2004 Peffly
2004/0235689 A1 11/2004 Sakai et al.
2005/0003975 A1 1/2005 Browne et al.
2005/0003980 A1 1/2005 Baker
2005/0020468 A1 1/2005 Frantz et al.
2005/0136011 A1 6/2005 Nekludoff
2005/0152863 A1 7/2005 Brautigam
2005/0192207 A1 9/2005 Morgan, III et al.
2005/0201967 A1 9/2005 Albrecht et al.
2005/0202984 A1 9/2005 Schwartz et al.
2005/0208106 A1 9/2005 Lange et al.
2005/0227902 A1 10/2005 Erazo-majewicz et al.
2005/0233929 A1 10/2005 Queen
2005/0245407 A1 11/2005 Ishihara
2005/0276831 A1 12/2005 Dihora
2006/0002880 A1 1/2006 Peffly
2006/0005333 A1 1/2006 Catalfamo et al.
2006/0009337 A1 1/2006 Smith
2006/0030509 A1 2/2006 Modi

(56) References Cited

U.S. PATENT DOCUMENTS

2006/0034778 A1 2/2006 Kitano et al.
2006/0057075 A1 3/2006 Arkin et al.
2006/0057097 A1 3/2006 Derici
2006/0079417 A1 4/2006 Wagner
2006/0079418 A1 4/2006 Wagner et al.
2006/0079419 A1 4/2006 Wagner et al.
2006/0079420 A1 4/2006 Wagner et al.
2006/0079421 A1 4/2006 Wagner et al.
2006/0084589 A1 4/2006 Vlad et al.
2006/0090777 A1 5/2006 Hecht et al.
2006/0094610 A1 5/2006 Yamato et al.
2006/0110415 A1 5/2006 Gupta
2006/0120982 A1 6/2006 Derici et al.
2006/0120988 A1 6/2006 Bailey et al.
2006/0135397 A1 6/2006 Bissey-beugras
2006/0159712 A1* 7/2006 Lee ........................ A61K 31/28 424/649
2006/0166857 A1 7/2006 Surburg et al.
2006/0171911 A1 8/2006 Schwartz et al.
2006/0182703 A1 8/2006 Arisz
2006/0183662 A1 8/2006 Crotty
2006/0210139 A1 9/2006 Carroll
2006/0229227 A1 10/2006 Goldman
2006/0252662 A1 11/2006 Soffin
2006/0263319 A1 11/2006 Fan et al.
2006/0269503 A1 11/2006 Yamazaki
2006/0276357 A1 12/2006 Smith et al.
2006/0292104 A1 12/2006 Guskey
2007/0003499 A1 1/2007 Shen et al.
2007/0020263 A1 1/2007 Shitara et al.
2007/0072781 A1 3/2007 Soffin et al.
2007/0110700 A1 5/2007 Wells
2007/0117737 A1 5/2007 Artiga et al.
2007/0154402 A1 7/2007 Trumbore et al.
2007/0155637 A1 7/2007 Smith et al.
2007/0160555 A1 7/2007 Staudigel
2007/0179207 A1 8/2007 Fernandez de Castro et al.
2007/0224152 A1 9/2007 Sakai
2007/0225193 A1 9/2007 Kuhlman et al.
2007/0269397 A1 11/2007 Terada
2007/0275866 A1 11/2007 Dykstra
2007/0292380 A1 12/2007 Staudigel
2007/0298994 A1 12/2007 Finke et al.
2008/0003245 A1 1/2008 Kroepke et al.
2008/0008668 A1 1/2008 Harichian et al.
2008/0019928 A1 1/2008 Franzke et al.
2008/0063618 A1 3/2008 Johnson
2008/0138442 A1 6/2008 Johnson
2008/0152610 A1 6/2008 Cajan
2008/0160093 A1 7/2008 Schwartz et al.
2008/0176780 A1 7/2008 Warr
2008/0194454 A1 8/2008 Morgan
2008/0206179 A1 8/2008 Peffly et al.
2008/0229512 A1 9/2008 Syed et al.
2008/0260655 A1 10/2008 Tamarkin et al.
2008/0260665 A1 10/2008 Guerchet et al.
2008/0261844 A1 10/2008 Ruppert et al.
2008/0299054 A1 12/2008 Chandar et al.
2008/0317698 A1 12/2008 Wells et al.
2009/0005280 A1 1/2009 Woo et al.
2009/0029900 A1 1/2009 Cetti et al.
2009/0041702 A1 2/2009 Molenda
2009/0062406 A1 3/2009 Loeffler
2009/0155383 A1 6/2009 Kitko et al.
2009/0178210 A1 7/2009 Bistram
2009/0197784 A1 8/2009 Ainger
2009/0221463 A1 9/2009 Kitko et al.
2009/0240223 A1 9/2009 Warren
2009/0246236 A1 10/2009 Kitko
2009/0312223 A1 12/2009 Yang et al.
2009/0312224 A1 12/2009 Yang et al.
2009/0324505 A1 12/2009 Seidling
2009/0324532 A1 12/2009 Okada et al.
2010/0000116 A1 1/2010 Aouad et al.
2010/0009285 A1 1/2010 Daems et al.
2010/0061946 A1 3/2010 Scherner et al.
2010/0087357 A1 4/2010 Morgan, III et al.
2010/0143280 A1 6/2010 Yokogi
2010/0152083 A1 6/2010 Velazquez
2010/0168251 A1 7/2010 Warr et al.
2010/0183539 A1 7/2010 Bernhardt
2010/0215775 A1 8/2010 Schmaus et al.
2010/0287710 A1 11/2010 Denutte et al.
2010/0310644 A1 12/2010 Liebmann
2010/0322878 A1 12/2010 Stella et al.
2011/0008267 A1 1/2011 Arkin et al.
2011/0023266 A1 2/2011 Gross et al.
2011/0098209 A1 4/2011 Smets et al.
2011/0107524 A1 5/2011 Chieffi et al.
2011/0118691 A1 5/2011 Nishitani
2011/0139170 A1 6/2011 Hippe et al.
2011/0150815 A1 6/2011 Woo et al.
2011/0165107 A1 7/2011 Derks et al.
2011/0171155 A1 7/2011 Federle
2011/0177017 A1 7/2011 Coffindaffer et al.
2011/0232668 A1 9/2011 Hoffmann et al.
2011/0245126 A1 10/2011 Tsaur et al.
2011/0245134 A1 10/2011 Smets
2011/0245136 A1 10/2011 Smets
2011/0268778 A1 11/2011 Dihora et al.
2011/0268802 A1 11/2011 Dihora
2011/0269657 A1 11/2011 Dihora
2011/0300095 A1 12/2011 Dente et al.
2011/0303766 A1 12/2011 Smith
2011/0305739 A1 12/2011 Royce
2011/0305778 A1 12/2011 Caggioni et al.
2011/0308555 A1 12/2011 Smets et al.
2011/0308556 A1 12/2011 Smets et al.
2012/0004328 A1 1/2012 Huchel et al.
2012/0009285 A1 1/2012 Wei et al.
2012/0031419 A1 2/2012 Batt
2012/0034173 A1 2/2012 Batt
2012/0052031 A1 3/2012 Troccaz et al.
2012/0100091 A1 4/2012 Hata et al.
2012/0100092 A1 4/2012 Murray
2012/0129924 A1 5/2012 Park et al.
2012/0219610 A1 8/2012 Smith, III et al.
2012/0230936 A1 9/2012 Mikkelsen
2012/0237469 A1 9/2012 Dente et al.
2012/0246851 A1 10/2012 Smith, III et al.
2012/0258150 A1 10/2012 Rauckhorst et al.
2012/0291911 A1 11/2012 Smith
2012/0309660 A1 12/2012 Kawasoe
2012/0316095 A1 12/2012 Wei et al.
2013/0029932 A1 1/2013 Kachi et al.
2013/0034515 A1 2/2013 Stone et al.
2013/0043145 A1 2/2013 Smith, III et al.
2013/0043146 A1 2/2013 Smith, III et al.
2013/0043147 A1 2/2013 Smith, III et al.
2013/0045285 A1 2/2013 Stella et al.
2013/0053295 A1 2/2013 Kinoshita et al.
2013/0053300 A1 2/2013 Scheibel et al.
2013/0071346 A1 3/2013 Okada
2013/0089586 A1 4/2013 Johnson et al.
2013/0089587 A1 4/2013 Staudigel
2013/0115173 A1 5/2013 Trumbore et al.
2013/0143784 A1 6/2013 Rizk
2013/0150338 A1 6/2013 Ananthapadmanabhan
2013/0156712 A1 6/2013 Frantz
2013/0189212 A1 7/2013 Jawale et al.
2013/0211952 A1 8/2013 Sugaya
2013/0216491 A1 8/2013 Ogihara et al.
2013/0243718 A1 9/2013 Pasquet
2013/0244922 A1 9/2013 Bartelt
2013/0266642 A1 10/2013 Hollingshead et al.
2013/0280202 A1 10/2013 Stella et al.
2013/0284195 A1 10/2013 Murdock
2013/0296289 A1 11/2013 Hall et al.
2013/0319463 A1 12/2013 Policicchio
2014/0037703 A1 2/2014 Dihora et al.
2014/0039066 A1 2/2014 Grimadell et al.
2014/0086893 A1 3/2014 Gutmann et al.
2014/0112879 A1 4/2014 Molenda et al.
2014/0127149 A1 5/2014 Lepilleur

(56) References Cited

U.S. PATENT DOCUMENTS

2014/0131395 A1 5/2014 Chang
2014/0134125 A1 5/2014 Dahl
2014/0162979 A1 6/2014 Palla-venkata
2014/0171471 A1 6/2014 Krueger
2014/0186864 A1 7/2014 Kato et al.
2014/0201927 A1 7/2014 Bianchetti et al.
2014/0216495 A1 8/2014 Bureiko
2014/0221269 A1 8/2014 Sobel et al.
2014/0228268 A1 8/2014 Fahl et al.
2014/0246515 A1 9/2014 Nakajima
2014/0308227 A1 10/2014 Mabille
2014/0348886 A1 11/2014 Johnson et al.
2014/0349902 A1 11/2014 Allef et al.
2015/0017152 A1 1/2015 Potechin et al.
2015/0021496 A1 1/2015 Shabbir
2015/0037273 A1 2/2015 Wagner
2015/0050231 A1 2/2015 Murase
2015/0057208 A1 2/2015 Frantz et al.
2015/0071977 A1 3/2015 Dihora
2015/0093420 A1 4/2015 Snyder
2015/0093429 A1 4/2015 Carter et al.
2015/0098921 A1 4/2015 Franzke et al.
2015/0099684 A1 4/2015 Boutique
2015/0108163 A1 4/2015 Smith et al.
2015/0110728 A1 4/2015 Jayaswal
2015/0141310 A1 5/2015 Smets et al.
2015/0147286 A1 5/2015 Barrera
2015/0157548 A1 6/2015 De Feij et al.
2015/0218496 A1 8/2015 Schmiedel et al.
2015/0231045 A1 8/2015 Krohn et al.
2015/0262354 A1 9/2015 Periaswamy
2015/0297489 A1 10/2015 Kleinen et al.
2015/0299400 A1 10/2015 Wagner et al.
2015/0313818 A1 11/2015 Stagg
2015/0352027 A1 12/2015 Thomas et al.
2015/0359725 A1 12/2015 Glenn, Jr. et al.
2015/0359726 A1 12/2015 Glenn, Jr. et al.
2015/0359728 A1 12/2015 Glenn, Jr. et al.
2016/0008257 A1 1/2016 Zhou et al.
2016/0022566 A1 1/2016 Figura
2016/0089317 A1 3/2016 Cetti et al.
2016/0089318 A1 3/2016 Cetti et al.
2016/0089322 A1 3/2016 Santos Nogueira et al.
2016/0089462 A1 3/2016 Frankenbach
2016/0089464 A1 3/2016 Frankenbach et al.
2016/0089465 A1 3/2016 Frankenbach et al.
2016/0090555 A1 3/2016 Frankenbach
2016/0090556 A1 3/2016 Frankenbach et al.
2016/0090557 A1 3/2016 Frankenbach et al.
2016/0090558 A1 3/2016 Frankenbach et al.
2016/0092661 A1 3/2016 Hollingshead et al.
2016/0095804 A1 4/2016 Xavier et al.
2016/0095808 A1 4/2016 Okada et al.
2016/0113849 A1 4/2016 Grimadell et al.
2016/0128944 A1 5/2016 Chawrai
2016/0143827 A1 5/2016 Castan Barberan et al.
2016/0193125 A1 7/2016 Jones et al.
2016/0206522 A1 7/2016 Ribaut et al.
2016/0235643 A1 8/2016 Mathonneau et al.
2016/0250115 A1 9/2016 Li et al.
2016/0279048 A1 9/2016 Jayaswal et al.
2016/0287503 A1 10/2016 Schroeder
2016/0287509 A1 10/2016 Peffly
2016/0296656 A1 10/2016 Scavone et al.
2016/0303043 A1 10/2016 Khoury
2016/0306909 A1 10/2016 Hollingshead et al.
2016/0309871 A1 10/2016 Torres Rivera et al.
2016/0310369 A1 10/2016 Thompson et al.
2016/0310370 A1 10/2016 Zhao et al.
2016/0310371 A1 10/2016 Zhao
2016/0310375 A1 10/2016 Torres Rivera
2016/0310386 A1 10/2016 Smith, III et al.
2016/0310388 A1 10/2016 Smith, III et al.
2016/0310389 A1 10/2016 Thompson et al.
2016/0310390 A1 10/2016 Smith, III et al.
2016/0310391 A1 10/2016 Smith, III et al.
2016/0310393 A1 10/2016 Chang et al.
2016/0310402 A1 10/2016 Zhao et al.
2016/0317424 A1 11/2016 Kadir
2016/0326458 A1 11/2016 Smets et al.
2016/0338929 A1 11/2016 Zasloff
2016/0354300 A1 12/2016 Thompson et al.
2017/0066579 A1 3/2017 Zillges
2017/0071837 A1 3/2017 Schelges et al.
2017/0101609 A1 4/2017 Vargas
2017/0110690 A1 4/2017 Lamansky et al.
2017/0110695 A1 4/2017 Nishikawa et al.
2017/0119917 A1 5/2017 Frankenbach et al.
2017/0137752 A1 5/2017 Frankenbach et al.
2017/0137753 A1 5/2017 Frankenbach et al.
2017/0165164 A1 6/2017 Zhao et al.
2017/0165165 A1 6/2017 Zhao et al.
2017/0209359 A1 7/2017 Zhao et al.
2017/0224607 A1 8/2017 Li et al.
2017/0239155 A1 8/2017 Hartnett
2017/0249407 A1 8/2017 Cetti et al.
2017/0249408 A1 8/2017 Cetti et al.
2017/0252273 A1 9/2017 Renock et al.
2017/0255725 A1 9/2017 Frankenbach et al.
2017/0273880 A1 9/2017 Hertenstein
2017/0278249 A1 9/2017 Stofel
2017/0283959 A1 10/2017 Shellef
2017/0304172 A1 10/2017 Chang et al.
2017/0304184 A1 10/2017 Glenn, Jr.
2017/0304185 A1 10/2017 Glenn, Jr. et al.
2017/0304186 A1 10/2017 Glenn, Jr.
2017/0326060 A1 11/2017 Matsuo
2017/0333321 A1 11/2017 Carnali
2017/0333591 A9 11/2017 Scavone et al.
2017/0367963 A1 12/2017 Kadir et al.
2018/0004875 A1 1/2018 Cetti et al.
2018/0044097 A1 2/2018 Zeik
2018/0057451 A1 3/2018 Owens et al.
2018/0066210 A1 3/2018 Frankenbach et al.
2018/0098923 A1 4/2018 Hutton, III
2018/0110594 A1 4/2018 Atkin
2018/0110688 A1 4/2018 Torres Rivera et al.
2018/0110689 A1 4/2018 Torres Rivera et al.
2018/0110690 A1 4/2018 Torres Rivera
2018/0110691 A1 4/2018 Torres Rivera et al.
2018/0110692 A1 4/2018 Torres Rivera et al.
2018/0110693 A1 4/2018 Renock et al.
2018/0110694 A1 4/2018 Renock et al.
2018/0110695 A1 4/2018 Thompson
2018/0110696 A1 4/2018 Johnson et al.
2018/0110704 A1 4/2018 Zhao et al.
2018/0110707 A1 4/2018 Zhao et al.
2018/0110710 A1 4/2018 Zhao et al.
2018/0110714 A1 4/2018 Glenn, Jr. et al.
2018/0116937 A1 5/2018 Park et al.
2018/0116941 A1 5/2018 Wang
2018/0133133 A1 5/2018 Kleinen et al.
2018/0177708 A1 6/2018 Lee et al.
2018/0221266 A1 8/2018 Zhao et al.
2018/0256481 A1 9/2018 Glenn, Jr.
2018/0280270 A1 10/2018 Rughani et al.
2018/0311135 A1 11/2018 Chang
2018/0311136 A1 11/2018 Chang
2018/0318194 A1 11/2018 Hoffmann et al.
2018/0344611 A1 12/2018 Zhao et al.
2018/0344612 A1 12/2018 Zhao et al.
2018/0344613 A1 12/2018 Zhao et al.
2018/0344614 A1 12/2018 Zhao et al.
2018/0360713 A1 12/2018 Jouy et al.
2019/0105242 A1 4/2019 Song
2019/0105243 A1 4/2019 Song et al.
2019/0105244 A1 4/2019 Song
2019/0105245 A1 4/2019 Song
2019/0105246 A1 4/2019 Cochran
2019/0105247 A1 4/2019 Song et al.
2019/0117543 A1 4/2019 Zhao
2019/0117544 A1 4/2019 Zhao
2019/0117545 A1 4/2019 Zhao
2019/0125650 A1 5/2019 Lee et al.

(56) References Cited

U.S. PATENT DOCUMENTS

2019/0142711 A1 5/2019 Torres Rivera
2019/0142800 A1 5/2019 Ghosh et al.
2019/0155975 A9 5/2019 Cetti et al.
2019/0167554 A1 6/2019 Wankhade
2019/0183777 A1 6/2019 Gillis
2019/0183778 A1 6/2019 Glenn, Jr.
2019/0192405 A1 6/2019 Zhao
2019/0240121 A1 8/2019 Torres Rivera
2019/0290553 A1 9/2019 Yokogi et al.
2019/0290554 A1 9/2019 Yokogi et al.
2019/0290562 A1 9/2019 Yokogi et al.
2019/0290567 A1 9/2019 Yokogi et al.
2019/0290568 A1 9/2019 Yokogi et al.
2019/0307298 A1 10/2019 Zhao
2019/0307665 A1 10/2019 Yokogi et al.
2019/0328647 A1 10/2019 Chang et al.
2019/0365611 A1* 12/2019 Brown ................ A61K 8/0241
2019/0365619 A1 12/2019 Ceballos et al.
2019/0365633 A1 12/2019 Glenn, Jr.
2020/0000690 A1 1/2020 Renock
2020/0078284 A1 3/2020 Botto et al.
2020/0113796 A1 4/2020 Yokogi
2020/0129402 A1 4/2020 Jamadagni
2020/0163846 A1 5/2020 Song
2020/0170894 A1 6/2020 Park et al.
2020/0188243 A1 6/2020 Brown et al.
2020/0197272 A1 6/2020 Hertenstein et al.
2020/0206110 A1 7/2020 Hertenstein et al.
2020/0237628 A1 7/2020 Torres Rivera
2020/0281843 A1 9/2020 Comeron
2021/0022986 A1 1/2021 Glenn, Jr.
2021/0093543 A1 4/2021 Parikh et al.
2021/0121385 A1 4/2021 Muller et al.
2021/0128444 A1 5/2021 Muller et al.
2021/0128447 A1 5/2021 Galpin et al.
2021/0169765 A1 6/2021 Renock
2021/0212927 A1 7/2021 Hutton, III et al.
2021/0267853 A1 9/2021 Johnson et al.
2021/0275410 A1 9/2021 Hutton, III
2021/0315791 A1 10/2021 Springob
2021/0353518 A1 11/2021 Ballhaus et al.
2021/0353522 A1 11/2021 Ballhaus et al.
2021/0401716 A1 12/2021 Gogineni et al.
2022/0062136 A1 3/2022 Feng
2022/0160606 A1 5/2022 Renock
2022/0175640 A1 6/2022 Herteinstein et al.
2022/0257066 A1 8/2022 Brown et al.
2022/0323337 A1 10/2022 Yamazaki
2022/0378680 A1 12/2022 Ballhaus et al.
2022/0378684 A1 12/2022 Cochran et al.
2022/0395444 A1 12/2022 Hutton, III
2022/0401327 A1 12/2022 Liu
2023/0053056 A1 2/2023 Renock et al.
2023/0105577 A1 4/2023 Chu
2024/0156700 A1 5/2024 Yokogi

FOREIGN PATENT DOCUMENTS

CA 704195 A 2/1965
CA 1248458 A 1/1989
CA 2078375 A1 3/1994
CN 1263455 A 8/2000
CN 1286612 A 3/2001
CN 1545404 A 11/2004
CN 1823929 A 8/2006
CN 100534415 C 9/2009
CN 101112349 B 5/2011
CN 101690697 B 10/2011
CN 101559034 B 1/2013
CN 102895151 A 1/2013
CN 102973437 A 3/2013
CN 102697668 B 8/2013
CN 103356408 A 10/2013
CN 102697670 B 7/2014
CN 104107401 A 10/2014
CN 102851015 B 12/2014
CN 105726393 A 7/2016
CN 105769617 A 7/2016
CN 106659664 A 5/2017
CN 106750361 A 5/2017
CN 107595657 A 1/2018
CN 107595673 A 1/2018
CN 107648096 A 2/2018
CN 107737329 A 2/2018
CN 107961212 A 4/2018
CN 108186385 A 6/2018
CN 108283583 A 7/2018
CN 108451858 A 8/2018
CN 110279591 A 9/2019
CN 110960434 A 4/2020
CN 113041184 A 6/2021
DE 2145204 A1 3/1973
DE 3018456 A1 11/1981
DE 4315396 A1 11/1994
DE 102004012009 A1 9/2005
DE 202005009618 U1 9/2005
DE 102004023720 A1 12/2005
DE 102014225083 A1 10/2015
DE 102014225606 A1 10/2015
DE 102015204987 A1 9/2016
EP 0108517 A2 5/1984
EP 0136914 A2 4/1985
EP 0574086 A2 12/1993
EP 0666358 A1 8/1995
EP 0674898 A2 10/1995
EP 1340485 A2 2/2003
EP 1346720 A2 9/2003
EP 0674898 B2 3/2006
EP 1714678 A1 10/2006
EP 1779838 A1 5/2007
EP 1337231 B1 8/2007
EP 1842572 A2 10/2007
EP 2005939 A1 12/2008
EP 1970045 A3 9/2009
EP 2394632 A1 12/2011
EP 2042216 B1 9/2015
EP 3121210 A1 1/2017
EP 3260171 A1 12/2017
EP 3522858 A1 8/2019
EP 3622946 A1 3/2020
ES 2052450 B1 12/1994
FR 2669531 A1 5/1992
FR 2795955 A1 1/2001
GB 190110699 A 8/1901
GB 191023922 A 10/1911
GB 487812 A 6/1938
GB 1347950 A 2/1974
GB 2048229 12/1980
GB 2450727 A 1/2009
HU 42318 7/1987
JP S56011009 A 12/1981
JP S58113300 A 7/1983
JP S58198412 A 11/1983
JP S60004598 A 1/1985
JP S61236708 A 10/1986
JP S62205200 A 9/1987
JP S63501221 A 5/1988
JP S63165308 A 7/1988
JP H04364114 A 12/1992
JP H06220495 A 8/1994
JP H0753340 A 2/1995
JP 07252134 A 10/1995
JP H08310924 A 11/1996
JP 09020618 A 1/1997
JP 09030938 A 2/1997
JP H09175961 A 7/1997
JP H10017894 A 1/1998
JP H11139944 A 5/1999
JP 2964226 B2 10/1999
JP 2000178586 A 6/2000
JP 3069802 B2 7/2000
JP 2001011492 A 1/2001
JP 2001011497 A 1/2001
JP 2001254099 A 9/2001

(56) References Cited

FOREIGN PATENT DOCUMENTS

| | | | |
|---|---|---|---|
| JP | 2001261529 | A | 9/2001 |
| JP | 2003201217 | A | 12/2001 |
| JP | 2002179552 | A | 6/2002 |
| JP | 2002226889 | A | 8/2002 |
| JP | 2002285191 | A | 10/2002 |
| JP | 2002336337 | A | 11/2002 |
| JP | 2003055699 | A | 2/2003 |
| JP | 2003082398 | A | 3/2003 |
| JP | 2003171688 | A | 6/2003 |
| JP | 2003176497 | A | 6/2003 |
| JP | 2003261413 | A | 9/2003 |
| JP | 2003268398 | A | 9/2003 |
| JP | 3480165 | B2 | 12/2003 |
| JP | 2003342131 | A | 12/2003 |
| JP | 3634988 | B2 | 3/2005 |
| JP | 3634991 | B2 | 3/2005 |
| JP | 3634996 | B2 | 3/2005 |
| JP | 2005187359 | A | 7/2005 |
| JP | 2005232113 | A | 9/2005 |
| JP | 2006063044 | A | 3/2006 |
| JP | 2006104149 | A | 4/2006 |
| JP | 2006124312 | A | 5/2006 |
| JP | 2006183039 | A | 7/2006 |
| JP | 2006193549 | A | 7/2006 |
| JP | 2006249092 | A | 9/2006 |
| JP | 2006282565 | A | 10/2006 |
| JP | 2007131687 | A | 5/2007 |
| JP | 2007177047 | A | 7/2007 |
| JP | 2007223935 | A | 9/2007 |
| JP | 2007238607 | A | 9/2007 |
| JP | 2007297380 | A | 11/2007 |
| JP | 2008001626 | A | 1/2008 |
| JP | 2008214292 | A | 9/2008 |
| JP | 2009096778 | A | 5/2009 |
| JP | 2009120559 | A | 6/2009 |
| JP | 2009161866 | A | 7/2009 |
| JP | 2010138130 | A | 6/2010 |
| JP | 2011153167 | A | 8/2011 |
| JP | 2011190221 | A | 9/2011 |
| JP | 2011241353 | A | 12/2011 |
| JP | 5041113 | B2 | 7/2012 |
| JP | 2013010757 | A | 1/2013 |
| JP | 2013091641 | A | 5/2013 |
| JP | 2013151434 | A | 8/2013 |
| JP | 2013155143 | A | 8/2013 |
| JP | 2013193968 | A | 9/2013 |
| JP | 2013216639 | A | 10/2013 |
| JP | 6046394 | B2 | 1/2014 |
| JP | 2014009177 | A | 1/2014 |
| JP | 2014024875 | A | 2/2014 |
| JP | 2014037383 | A | 2/2014 |
| JP | 2014091723 | A | 5/2014 |
| JP | 2014234350 | A | 12/2014 |
| JP | 5667790 | B2 | 2/2015 |
| JP | 2015034157 | A | 2/2015 |
| JP | 2015101545 | A | 6/2015 |
| JP | 2015129099 | A | 7/2015 |
| JP | 2016013973 | A | 1/2016 |
| JP | 2016030722 | A | 3/2016 |
| JP | 2016088910 | A | 5/2016 |
| JP | 6184550 | B1 | 8/2017 |
| JP | 2018012673 | A | 1/2018 |
| JP | 2018083781 | A | 5/2018 |
| KR | 100290589 | B1 | 9/2001 |
| KR | 100821846 | B1 | 4/2008 |
| KR | 1020080111280 | A | 12/2008 |
| KR | 20090095359 | A | 9/2009 |
| KR | 20100040180 | A | 4/2010 |
| KR | 20140060882 | A | 5/2014 |
| KR | 101494008 | B1 | 2/2015 |
| KR | 101503922 | B1 | 3/2015 |
| KR | 101532070 | B1 | 7/2015 |
| UA | 50333 | U | 5/2010 |
| WO | 8603679 | A1 | 7/1986 |
| WO | 9114759 | A1 | 10/1991 |
| WO | 91017237 | A1 | 11/1991 |
| WO | 9213520 | A1 | 8/1992 |
| WO | 199325650 | A1 | 12/1993 |
| WO | 9417783 | A2 | 8/1994 |
| WO | 9502389 | A2 | 1/1995 |
| WO | 9714406 | A2 | 4/1997 |
| WO | 9726854 | A1 | 7/1997 |
| WO | 9823258 | A1 | 6/1998 |
| WO | 9906010 | A2 | 2/1999 |
| WO | 9918928 | A1 | 4/1999 |
| WO | 9924004 | A1 | 5/1999 |
| WO | 9924013 | A1 | 5/1999 |
| WO | 9949837 | A1 | 10/1999 |
| WO | 9957233 | A1 | 11/1999 |
| WO | 0012553 | A1 | 3/2000 |
| WO | 0032601 | | 6/2000 |
| WO | 0119949 | A1 | 3/2001 |
| WO | 0142409 | A1 | 6/2001 |
| WO | 0148021 | A1 | 7/2001 |
| WO | 2001076552 | A2 | 10/2001 |
| WO | 2003051319 | A1 | 6/2003 |
| WO | 03096998 | A1 | 11/2003 |
| WO | 03105793 | A2 | 12/2003 |
| WO | 2004078901 | A1 | 9/2004 |
| WO | 2005023975 | A1 | 3/2005 |
| WO | 2008017540 | A1 | 2/2008 |
| WO | 2008128826 | A1 | 10/2008 |
| WO | 2008145582 | A1 | 12/2008 |
| WO | 2009016555 | A2 | 2/2009 |
| WO | 2009030594 | A1 | 3/2009 |
| WO | 2009053931 | A2 | 4/2009 |
| WO | 2010026009 | A1 | 3/2010 |
| WO | 2010052147 | A2 | 5/2010 |
| WO | 2011124560 | A2 | 10/2011 |
| WO | 2012017091 | A2 | 2/2012 |
| WO | 2012052536 | A2 | 4/2012 |
| WO | 2012055587 | A1 | 5/2012 |
| WO | 2012055812 | A1 | 5/2012 |
| WO | 2012084970 | A1 | 6/2012 |
| WO | 2012127009 | A1 | 9/2012 |
| WO | 2012136651 | A1 | 10/2012 |
| WO | 2013010706 | A2 | 1/2013 |
| WO | 2013018805 | A1 | 2/2013 |
| WO | 2013119908 | A1 | 8/2013 |
| WO | 2014073245 | A1 | 5/2014 |
| WO | 2014073456 | A1 | 5/2014 |
| WO | 2014111667 | A2 | 7/2014 |
| WO | 2014111668 | A2 | 7/2014 |
| WO | 2014148245 | A1 | 9/2014 |
| WO | 2015016037 | A1 | 2/2015 |
| WO | 2015067779 | A1 | 5/2015 |
| WO | 2015085376 | A1 | 6/2015 |
| WO | 2015122371 | A1 | 8/2015 |
| WO | 2015141787 | A1 | 9/2015 |
| WO | 2016049389 | A1 | 3/2016 |
| WO | 2016054347 | A1 | 4/2016 |
| WO | 2016147196 | A1 | 9/2016 |
| WO | 2017052161 | A1 | 3/2017 |
| WO | 2017140798 | A1 | 8/2017 |
| WO | 2017140802 | A1 | 8/2017 |
| WO | 2017207685 | A1 | 12/2017 |
| WO | 2018023180 | A1 | 2/2018 |
| WO | 2018064511 | A1 | 4/2018 |
| WO | 2018109148 | A1 | 6/2018 |
| WO | 2018191567 | A1 | 10/2018 |
| WO | 2018191573 | A1 | 10/2018 |
| WO | 2019030458 | A2 | 2/2019 |
| WO | 2019074990 | A1 | 4/2019 |
| WO | 2019074992 | A1 | 4/2019 |
| WO | 2019200027 | A1 | 10/2019 |
| WO | 2020005309 | A1 | 1/2020 |
| WO | 2020030732 | A1 | 2/2020 |
| WO | 2020076881 | A1 | 4/2020 |
| WO | 2020131836 | A1 | 6/2020 |
| WO | 2021026572 | A1 | 2/2021 |
| WO | 2021099088 | A1 | 5/2021 |
| WO | 2021127318 | A1 | 6/2021 |
| WO | 2021144326 | A1 | 7/2021 |

(56) References Cited

FOREIGN PATENT DOCUMENTS

WO 2021231510 A1 11/2021
WO 2022144161 A1 7/2022
WO 2024037872 A1 2/2024

OTHER PUBLICATIONS

"Hydrating Conditioner Bar" Mintel Database, Retrieved from the internet: https://www.gnpd.com, Aug. 1, 2018, 4 Pages.
"Jaguar® Optima", Solvay, site: www.solvay.com, year 2023, 1 page.
"Natural Detangling Shampoo", Mintel Database, dated Sep. 13, 2017; 2 pages.
"Personal care solutions Guide", Solvay, Publication date: May 2018, 84 pages.
"Soda Shampoo", Mintel Database, dated Apr. 2015; pp. 1-4.
"Treatment Foam for Recurrent Scaling Conditions", Mintel Database, Aug. 2007; pp. 1-2.
16544M PCT Search Report and Written Opinion for PCT/US2024/035934; dated Oct. 29, 2024, 16 pages.
Acne Foaming Cleanser, Database accession No. 4172863, Jul. 29, 2016, 3 pages.
Air Quality of the Iowa Department of Natural Resources. A Review of The Science and Technology of Odor Measurement, 2005, 51 pages (2005).
All Office Actions;U.S. Appl. No. 16/595,755, filed Oct. 8, 2019.
All Office Actions; U.S. Appl. No. 18/204,179, filed May 31, 2023.
All Office Actions; U.S. Appl. No. 18/422,155, filed Jan. 25, 2024.
Anonymous, "Healing + Anti-Breakage Shampoo", ID# 3383875, Mintel GNPD, URL: http://www.gnpd.com, dated Aug. 2015, 3 pages.
Anonymous, "Medicated Cleanser", Nioxin Research Laboratories, Mintel GNPD [online], ID:1060983, URL: http://www.gnpd.com, dated Feb. 2009, 4 pages.
Anonymous, "Shampoo", ID# 1743027, Mintel GNPD, URL: http://www.gnpd.com, dated Mar. 2012, 3 pages.
Anonymous: "Merquat Polyquaternium 47 Series, Water Soluble Polymers for Personal Care", Jul. 30, 2017, URL: https://www.in-cosmetics.com/_novadocuments/2729, retrieved on Dec. 21, 2018 ; 1 page.
Anonymous: "Acne Foaming Cleanser", Database GNPD [Online] Mintel, XP055591421, Jul. 29, 2016, 03 Pages.
Anonymous: "Anti-Dandruff Scalp Care Shampoo", Mintel, Database accession No. 301924, Sep. 16, 2004, 2 pages.
Anonymous: "Anticaspa-Graso Anti-Dandruff Shampoo",Database GNPD [Online] Mintel; XPC:I55787029, Database accession No. 351776paragraph [ingredients], Apr. 5, 2005 (Apr. 5, 2005).
Anonymous: "Naturally Derived Body Wash", Database GNPD [Online] Mintel; Feb. 15, 2021, 2 pages.
Anonymous: "Naturally Rich Moisturizing Shampoo", Database GNPD [Online] Mintel, XP55897729, Mar. 27, 2019, 03 Pages.
Anonymous: "Peptide Shampoo", Database GNPD [Online] Mintel; Dec. 14, 2015, 3 pages.
Anonymous: "Replenishing Moisture Shampoo", Database GNPD [Online] Mintel, Mar. 10, 2015.
Anonymous: "Shampoo C", Database GNPD [Online] Mintel, Sep. 29, 2011, 03 Pages.
Anonymous: "Shampoo", Database GNPD [Online] Mintel, Jan. 26, 2021, 3 pages.
Anonymous: "Shampooing au Phytolait d'abricot-Formule N°102-MP06-MI3-AA03", Internet Citation, Feb. 19, 2005, Retrieved from the Internet: URL: http://web.archive.org/web/20050219040350/www.albanmuller.com/francais/catalogue/formules/formul10.asp, 1 page.
Anonymous; "Advanced Oil Control Anti Dandruff Shampoo", XP093149356, Database GNPD Mintel, Database accession No. 9347772, dated Feb. 1, 2022, 03 Pages.
Anonymous; "Shampoo", ID: 7162235, Database GNPD [Online] Mintel; dated Jan. 6, 2020, 3 pages.
ASTM D3954-94, Reapproved 2010, vol. 15.04, Standard Test Method for Dropping Point of Waxes.
BASF, "Practical Guide to Rheology Modifiers", download from https://insights.basfcom/files/BASF_ED_RheologyModifiers_download.pdf on Nov. 1, 2022. (Year: 2022).
Brattoli et al. Odour Detection Methods: Olfactometry and Chemical Sensors. Sensors (Basel), 2011; 11(5); 5290-5322 (2011).
Bryant Taylor, "Here's What You Need to Know About the Latest Korean Beauty Obsession", Retrieved from Internet: https://www.refinery29.com/en-us/scalp-ph-facts, Jun. 5, 2016, 8 pages.
Cafasso, "What's the proper order to use shampoo and conditioner while bathing", Healthline, Retrieved from Internet: https://www.healthline.com/health/beauty-skin-care/shampoo-or-conditioner-first, dated Jul. 13, 2020, 2 pages.
Carbopol Aqua SF-1 Polymer Technical Data Sheet, TDS-294, dated Dec. 2000 ; pp. 1-9.
Chemical Book, Isolongifolone, available at http://www.chemicalbook.com/ProductChemicalPropertiesCB5318980_EN.htm, Copyright 2016, 1 page.
Christensen et al., "Experimental Determination of Bubble Size Distribution in a Water Column by Interferometric Particle Imaging and Telecentric Direct Image Method", Student Report, Aalborg University; dated Jun. 3, 2014; 123 pages.
Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.
CTFA Cosmetic Ingredient Dictionary, 1982, 3rd Edition, The Cosmetic, Toiletry & Fragrance Association, Inc., Washington, DC (book not included).
D'Souza et al., Shampoo and Conditioners: What a Dermatologist Should Know? Indian J Dermatol, dated May-Jun. 2015; pp. 60(3), 248-254 (2015).
Database GNPD [Online] Mintel; Mar. 28, 2018 (Mar. 28, 2018), anonymous:Dandruff Control Shampoo 11, XP055787038, Database accession No. 5556267, abstract.
Datasheet: Empigen Total Active TC/U, Datasheet, dated Jan. 31, 2017 (Innospec) ; 2 pages.
Dehyquart Guar: Published dated Nov. 2010 ; pp. 1-34.
Duis et al., "Environmental fate and effects of water-soluble synthetic organic polymers used in cosmetic products", Enviromental Sciences Europe, 33:21, Year 2021; 20 pages.
Fevola, Michael J. "Guar Hydroxypropyltrimonium Chloride." Cosmetics and toiletries; vol. 127.1; Jan. 2012 ; pp. 16-21.
Goh et al, "New cationic conditioning polymers for hair care", Retrieved from Internet: https://cosmeticsbusiness.com/new-cationic-conditioning-polymers-for-hair-care-47152, Dec. 18, 2006, 10 pages.
Grillet et al., "Polymer Gel Rheology and Adhesion", Rheology, 2012, pp. 59-80.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from theInternet: URL:https://www.happi.com/contents/view_formulary/2009-10-01/sulfate-free-surfactants-conditioning-shampoo/, XP002804301, Jan. 10, 2019, 1 page.
Hossel et al. "Conditioning polymers in today's shampoo formulations—efficacy, mechanism and test methods", International Journal of Cosmetic Science. 2000, vol. 1, 2000, pp. 1-10.
Inspection certificate for Hostapon® CCG, Clariant Ibérica Production, S.A., May 6, 2019; p. 1-2.
Manuel, F. et al., A new postulate on two stages of dandruff: A clinical perspective, International Journal of Trichology, 2011, vol. 3, 3-6 (Year: 2011).
Matsouka et al., "Vesicle formation of disodium lauryl sulfosuccinate", Journal of Molecular Liquids, 348, 118422, Nov. 1, 2021, 7 pages.
McGinley et al., "Performance Verification of Air Freshener Products and Other Odour Control Devices for Indoor Air Quality Malodours", Presented at the 8th Workshop on Odour and Emissions of Plastic Materials Universitat Kassel Institut for Wesrkstofftechnik Kassel, Germany, Mar. 27-28, 2006, 13 pages.

(56) References Cited

OTHER PUBLICATIONS

McGinley et al., American Association of Textile Chemists and Colorists, year 2017, 16 pages.
Medvedev, Diffusion Coefficients in Multicomponent Mixtures, PHD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Morioka, H. et al. "Effects of Zinc on the New Preparation Method of Hydroxy Double Salts" Inorg. Chem. 1999, 38, 4211-6.
Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, 366-371 (Year: 2013).
P. A. Cornwell, "A review of shampoo surfactant technology: consumer benefits, raw materials and recent developments", International Journal of Cosmetic Science, 40 , Oct. 27, 2017, pp. 16-30.
Parchem fine & specialty chemicals. MIPA-laureth sulfate supplier distributor—CAS 83016-76-6; dated 2021; pp. 1-7.
Perm Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-theSafety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Record Tego® Betain F KB 5, dated Jul. 1, 2015, 4 pages.
Product Data Sheet for Chemoryl™ MLS Surfactant, Sodium Lauroyl Sarcosinate, Lubrizol Advanced Materials, Inc.,Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018;2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
PubChem CID 3033856 for decyl glucoside. downloaded Jun. 22, 2023, 32 pages. (Year: 2023).
Rajendran A. et al: "Study on the Analysis of Trace Elements in Aloe veraand Its Biological Importance Study on the Analysis of Trace Elements in Aloe vera and Its Biological Importance", Journal of Applied Sciences Research, Jan. 1, 2007 (Jan. 1, 2007) pp. 1476-1478.
Ramachandra et al, "Processing of Aloe Vera Leaf Gel: A Review", American Journal of Agricultural and Biological Sciences 3 (2), year 2008, pp. 502-510.
Robinson et al.,Final Report of the Amended Safety Assessment of Sodium Laureth Sulfate and Related Salts of SulfatedEthoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics , dated Sep. 20, 2013, 46 pages.
Sbhatu et al, "Formulation and Physicochemical Evaluation of Lab-Based Aloe adigratana Reynolds Shampoos", Hindawi, International Journal of Analytical Chemistry, vol. 2020, Article ID 6290617, URL: https://www.ncbi.nlm.nih.gov/pmc/articles/PMC7160718/, Published Apr. 4, 2020, 7 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Sensory.,"A Review of the Science and Technology of Odor Measurement", Prepared for the Air Quality Bureau of the lowa Department of Natural Resources, Dec. 30, 2005 51 pages.
Shampoo C, Database accession No. 1632217, Sep. 29, 2011, 3 pages.
Shampoo Manufacturing Plant, Lodha International, URL: https://www.lodhapharma.com/shampoo-manufacturing-plant.php#: ~:text=Shampoos%20are%20categorized%20as%20viscous,if%20not%20all%20of%20them, Published: 2018, 4 pages.
Shampoo, ID# 6148479, Mintel GNPD [online], URL: http://www.gnpd.com, Nov. 2018, 4 pages.
Softazoline CL-R, Kawaken Singapore PTE Ltd. Website printout from http://kawaken.com.sg/softazoline-ch-r//a, accessed on Nov. 30, 2022.
Tarun et al. "Evaluation of pH of Bathing Soaps and Shampoos for Skin and Hair Care", Indian Journal of Dermatology. 2014, vol. 59, No. 5, No Known Date, 6 Pages.
Technical Information; TEGO® Betain F KB 5 / TEGO® Betain F KM 1; Mild amphoteric surfactants: www.evonik.com/personal-care; Jul. 2010; 2 pages; Product Specification; 5 pages.
Todd et al., Volatile Silicone Fluids for Cosmetics, Cosmetics and Toiletries, vol. 91, pp. 27-32 (Jan. 1976).
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates and Guidelines of Corona Virus View project health and beauty science View project Rohit Bhavsar Reliance Industries Limited; International Journal for Research inApplied Science & Engineering Technology, Apr. 1, 2020 (Apr. 1, 2020) XP055842327,DOI: 10.22214, 14 pages.
Yang et al., "Synthesis and foaming performance of Lauramidopropyl Betaine Derivate Surfactants", Materials Science Forum, vol. 953, Jan. 9, 2019, 1 page.
"Deep Image Matting", Ning Xu et al, Beckman Institute for Advanced Science and Technology, University of Illinois at Urbana-Champaign, Adobe Research, dated Mar. 10, 2017; 10 pages.
"Selecting the Right Surfactant for Cosmetics", Retrieved from Internet: https://cosmetics.specialchem.com/centers/selecting-the-right-surfactantforcosmetics/surfactantsinhaircareapplications#:~:text=Amphoteric%20surfactants%20are%20used%20to,be%20based%20ntirely%20on%20amphoterics, Aug. 11, 2020, 4 pages.
"UltraPureGel", Retrieved from Internet: https://www.ingredientstodiefor.com/item/UltraPureGel/1264, Jul. 29, 2012, 4 pages.

* cited by examiner

Fig. 1 – Initial Appearance
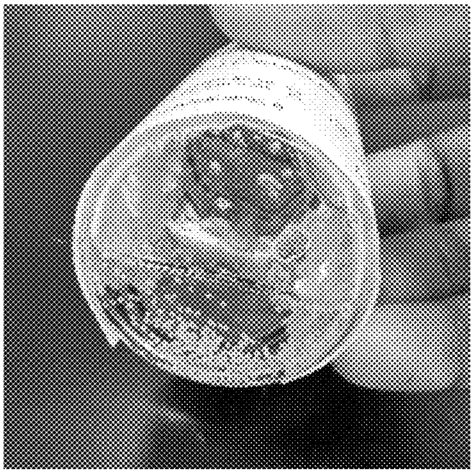
Fig. 2 – Inventive Example after 4 Week Stability Test
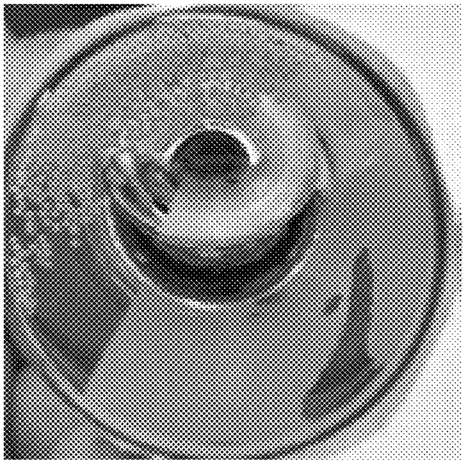
Fig. 3 – Comparative Example after 4 Week Stability Test
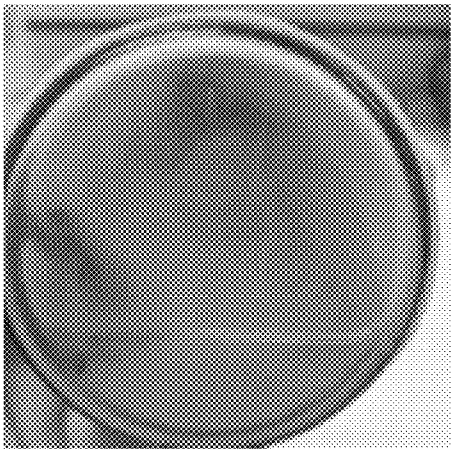

PRODUCT COMPOSITION COMPRISING A DISCRETE PARTICLE AND A NON-AQUEOUS BASE

FIELD

The present disclosure relates generally to a personal care composition containing discrete particles of a mixture composition and a non-aqueous base. More specifically, the present disclosure relates to discrete particles of a mixture composition comprising a surfactant and a high melting point fatty compound dispersed in a non-aqueous base comprising at least 75% of a fluid that is not a hydrogen donor.

BACKGROUND

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits by deposition of the traditional gel network within an aqueous chassis.

Another approach widely used by consumers is to apply hair oils or other anhydrous products to wet or dry hair to improve their manageability and softness. But these hair oils do not include the benefits provided by the cationic surfactants and fatty compounds.

Thus, there is a continuing need for non-aqueous hair care compositions that can still deliver the conditioning benefits that consumers want and expect.

SUMMARY

A product composition comprising a discrete particle of a mixture composition, wherein the mixture composition comprises a surfactant and a high melting point fatty compound; and a non-aqueous base, wherein the non-aqueous base comprises at least 75% of a fluid that is not a hydrogen donor.

BRIEF DESCRIPTION OF THE FIGURES

FIG. 1 is a photograph of the initial appearance of an inventive composition.

FIG. 2 is a photograph of the appearance of an inventive composition after the 4 Week Stability Test.

FIG. 3 is a photograph of the appearance of a comparative composition after the 4 Week Stability Test.

DETAILED DESCRIPTION

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

All ingredient percentages described herein are by weight of the cosmetic composition, unless specifically stated otherwise, and may be designated as "wt %." All ratios are weight ratios, unless specifically stated otherwise. All such percentages or weights as they pertain to listed ingredients are based on the active level and, therefore, do not include carriers or by-products that may be included in commercially available materials. The number of significant digits conveys neither a limitation on the indicated amounts nor on the accuracy of the measurements. Unless otherwise indicated, all measurements are understood to be made at approximately 25 °C and at ambient conditions, where "ambient conditions" means conditions under 1 atmosphere of pressure and at 50% relative humidity. All ranges are inclusive and combinable. For example, all numeric ranges are inclusive of narrower ranges, and delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

"About" modifies a particular value by referring to a range of plus or minus 20% or less of the stated value (e.g., plus or minus 15% or less, 10% or less, or even 5% or less).

"Mixture" means a simple combination of materials and any compounds that may result from their combination.

"Molecular weight" means the weight average molecular weight, unless otherwise stated. Molecular weight can be measured using industry standard method, gel permeation chromatography ("GPC").

"Non-aqueous" means a material or composition contain less than 10% water (e.g., less than 5%, 3%, 1%, or 0.5%, or in some cases 0% water).

"Hydrogen donor" or "hydrogen bond donor" means a compound or functional group that has a hydrogen atom bonded to an oxygen, nitrogen, fluorine, chlorine, or sulfur atom.

"Solid" means that the anhydrous discrete particle does not conform to the shape of the container in which the particle is held at 25 °C.

"Substantially free of" means 2% or less (e.g., less than 1%, 0.5% or even less than 0.1%) of a stated material or ingredient. "Free of" means no detectable amount of the stated material or ingredient.

Personal Care Composition

Conventional aqueous-based hair care products such as shampoos and conditioners generally deliver hair care cleaning and conditioning benefits that consumers expect. In some instances, consumers are known to apply conditioning oils to hair in a pre-wash and/or post-wash step. Pre-wash oil application is believed to nourish hair and protect it during the wash process. Post-wash oil application may be done for manageability and styling.

The personal care compositions disclosed herein contain discrete particles of a mixture composition dispersed in a non-aqueous carrier. The present products can provide more flexibility than conventional gel network compositions, improved visual/aesthetic appearance, improved stability, especially when using smaller amounts of actives such as surfactants and high melting point fatty compounds, and improved deposition of benefit agents. Desirably, the stability improvement can be obtained without the use of a thickening polymer.

The personal care product herein can be a hair care product, a body care product composition, a facial skin care product, and mixtures thereof. In some instances, the personal care product is a hair conditioning product (e.g., a conditioning shampoo or a conditioner). The personal care compositions herein can be in the form of rinse-off products or leave-on products and can be formulated in a wide variety of product forms, including but not limited to oils, gels, emulsions, mousses and sprays. The personal care compositions herein may be used for the non-therapeutic treatment of hair such as, for example, cleaning and/or conditioning. The personal care composition may be particularly suitable for use as a hair conditioner, especially a leave-on hair oil.

In some instances, the personal care product can be free of or substantially free of detersive surfactants. The detersive surfactants herein are those selected from anionic surfactants, zwitterionic surfactant, amphoteric surfactant, and combinations thereof.

Mixture Composition

The mixture composition herein comprises a surfactant, a high melting point fatty compound and, optionally, a benefit agent. The surfactant and high melting point fatty compound are described in more detail below. The mixture composition may be added to a product composition at a level of 0.01% to 70% (e.g., 0.01% to 50% or 0.05% to 30%), in view of having discrete particles of the mixture composition in the non-aqueous base composition and in the product composition, and also in view of providing at least one the followings: more flexibility and stability in the product composition; improved deposition of benefit agents; and improved visual/aesthetic appearance.

The surfactant(s) and the high melting point fatty compound(s) may be present in the mixture composition, with or without other ingredients, at 10% to 99.9% (e.g., 20% to 99.9%, 40% to 99.9%, 60% to 99.9%, 80% to 99.9% or to even 100%), based on the weight of the mixture composition, in view of having discrete particles of the mixture composition in the non-aqueous base composition and in the personal care composition while containing other ingredients such as benefit agents, and also in view of providing at least one the followings: more flexibility in the product composition; improved stability in the product composition; improved deposition of benefit agents; and improved visual/aesthetic appearance.

Other than the surfactants and high melting point fatty compounds, when the mixture composition contains any liquid such as water-insoluble, water-miscible, and water-soluble liquids and water, it is also preferred to control the level of such liquids, so that the total liquid level in the mixture composition can be up to 30%, 40%, 50%, 60% or even up to 92%, by weight of the mixture composition, in view of having discrete particle of the mixture composition in the non-aqueous base composition and in the product composition.

When the liquid is water insoluble liquid such as a silicone oil, a water miscible liquid such as propylene glycol or glycerin, or a water-soluble liquids such as isopropyl alcohol (IPA) or ethanol, such liquid can be contained in the mixture composition at a level by weight of the mixture composition of up to 30%, 40%, 50%, 60%, or even up to 90%.

When the mixture composition contains water, it may be desirable to limit the level of water to less than 50% (e.g., less than 25%, 15%, 10%, or even less than 8%), by weight of the mixture composition, in view of having discrete particles of the mixture composition in the non-aqueous base composition and in the product composition.

The surfactant and the high melting point fatty compound may be included in the mixture composition such that the weight ratio of the surfactant to the high melting point fatty compound is in the range of 1:1 to 1:30 (e.g., 1:10 to 1:30 or 1:10 to 1:20) to provide a suitable conditioning benefit.

Benefit Agent for the Mixture Composition

The mixture composition may further comprise a benefit agent in addition to the surfactant and the high melting point fatty compound. The benefit agent may be present in the mixture composition at a level by the weight of the mixture composition, of 0.1% to 90% (e.g., 0.3% to 60%, 0.5% to 40%, or even 0.5% to 30%) in view of providing benefits from the benefit agents and in view of having discrete particle of the mixture composition in the non-aqueous composition and in the product composition.

Some non-limiting examples of benefit agents that may be suitable for use herein include silicone compounds, perfumes (e.g., conventional perfumes or perfume micro capsules (PMC), in which perfume is encapsulated by a polymeric outer layer), coloring agents (e.g., pigments or dyes that provide the discrete particle with a color that is different from the color of the non-aqueous base composition), agents which are incompatible to at least one ingredient contained in the mixture composition, discrete particle and/or non-aqueous base composition ("incompatible agents"), and mixtures thereof. In some embodiments the incompatible agent may be a solid mineral or chemical substance that has a high ionic strength and/or high surface charge and tends to cause agglomeration and/or crystallization (e.g., mica, salicylic acid, zinc pyrithione, and/or an organic oil material that undesirably interacts with a gel network component such as, for example, hexyldecanol and isostearyl isostearate).

When the mixture composition contains a silicone or perfume benefit agent, the mixture compositions may be contained in the personal care composition at a level of 0.1% to 70% (e.g., 0.5% to 50%, 1% to 30%, or even 2% to 20%). When the mixture composition contains a coloring agent or mica benefit agent, the mixture compositions may be contained in the product composition at 0.01% to 50% (e.g., 0.01% to 30%, 0.01% to 20% or 0.05% to 10%).

Non-Aqueous Base

The personal care compositions herein include a non-aqueous base, wherein at least 75% (e.g., at least 80%, 85%, 90% or even 95% or more) of the non-aqueous base is a fluid(s) that is not a hydrogen donor. In some embodiments, the fluid of the non-aqueous base may be 100% of a fluid that is not a hydrogen donor, for example, a single fluid material that is not a hydrogen donor.

Previously, combinations of a surfactant and a high melting point fatty compound as a discrete particle within a base composition were done in an aqueous carrier. One reason was it was believed that the particles would not be able to be maintained as discrete particles, but that they would disintegrate too quickly due to the relatively high solubility of the fatty compound in the non-aqueous carrier.

With the choice of certain non-aqueous bases, it has surprisingly been found that the discrete particle can maintain its integrity. The present inventors have now discovered that when the non-aqueous base is substantially made up of a material that is not a hydrogen donor, the discrete particle described herein is not dissolved within the non-aqueous base. The choice of a non-aqueous base that comprises at least 75% of a fluid that is not a hydrogen donor, when combined with the discrete particle, allows the particle to resist disintegration over time. For example, the particle will not exhibit any significant disintegration within 4 weeks if placed in elevated temperature conditions (e.g., 40 °C).

The non-aqueous base composition comprises at least 75% of a fluid that is not a hydrogen donor, and the fluid may be an oil. The present inventors have found that not all oils are able to be part of a conditioning formulation that does not disintegrate the discrete particles. They have discovered that oils that are not a hydrogen donor are able to be formulated successfully. Also relevant is the AlogP of the fluid. Fluids that successfully formulate while not disintegrating the discrete particle (as defined by the 4 Week Stability Test Method) include those that have an AlogP of at least 6.

The fluid of the non-aqueous base may be an oil, in some cases a low melting point oil, defined herein as oils having a melting point of 27 °C or lower (e.g., 25 °C or lower). Some non-limiting examples of a low melting point oils useful herein include 1-decanol, isohexadecane, isododecane, triethylhexanoin, isodecyl oleate, decyl oleate, silicone quaternium-26, dimethicone, hydrocarbons having 10 to 40 carbon atoms, unsaturated fatty alcohols having 10 to 30 carbon atoms such as oleyl alcohol; unsaturated fatty acids having 10 to 30 carbon atoms; fatty acid derivatives; fatty alcohol derivatives; ester oils (e.g., pentaerythritol ester oils such as pentaerythritol tetraisostearate), trimethylol ester oils, citrate ester oils, glyceryl ester oils, poly α-olefin oils such as polydecenes; and mixtures thereof.

Additional appropriate oils may include triglycerides, such as caprylic capric triglyceride or vegetable oils such as coconut oil, soybean oil, rapeseed oil, cocoa butter, olive oil, palm oil, rice bran oil, and mixtures thereof.

Additional fluids of the non-aqueous base may include, but are not limited to, hydrocarbons, branched hydrocarbons, more specifically an alkane, such as C13-C16 isoparaffin, isohexadecane, pentadecane, isododecane, C15-19 alkane, C9-12 alkane, C13-15 alkane, C14-22 alkane, coconut alkanes.

Also appropriate for use as the non-aqueous fluid may be an ester, including, but not limited to, isobutyl palmitate, isodecyl oleate, decyl oleate, oleyl oleate, triethylhexanoin, isopropyl isostearate, isostearyl isostearate, myristyl myristate, isopropyl myristate, propylene glycol dicaprate, diethylhexyl adipate.

The fluid of the non-aqueous base may, or may not, be or comprise a silicone compound. It is believed that the silicone compound can provide smoothness and softness on dry hair. The silicone compounds herein can be used at levels by weight of the composition, or by weight of the non-aqueous base, of 0.1%-99%.

Benefit Agent for the Non-Aqueous Base Composition

The non-aqueous base composition may include 0.05% to 60% (e.g., 0.1% to 30%, 0.1% to 20%, or 0.1% to 10%), by the weight of the non-aqueous base composition, of a benefit agent. The benefit agent may be present in the personal care composition at 0.05% to 30% (e.g., 0.1% to about 15%, 0.1% to 10%, or 0.1% to about 7%), by weight of the personal care composition.

Some non-limiting examples of benefit agents that may be suitable for use herein include silicone compounds, perfumes (e.g., conventional perfumes or perfume micro capsules (PMC), in which perfume is encapsulated by a polymeric outer layer), coloring agents (e.g., pigments or dyes that provide the non-aqueous base with a color that is different from the color of the discrete particles), incompatible agents, and mixtures thereof.

Depending on the type of the benefit agent, when containing the benefit agent, the personal care composition may provide at least one of the following benefits: improved deposition of benefit agents and improved stability when containing incompatible agents.

Discrete Particle

The personal care compositions herein contain discrete particles of the mixture composition. The discrete particles are dispersed in the non-aqueous base composition and can be visually observed as discrete particle in final product composition visually. For example, the particles can be observed by an unaided human eye with 20/20 vision at a distance of 25 cm in typical day time lighting.

The discrete particles are contained in the product composition at a level by weight of the product composition, of 0.1% to 70% (e.g., 0.1% to 50% or 0.1% to 30%), in view of providing at least one the followings: more flexibility in the product composition; improved stability in the product composition; improved deposition of benefit agents; and improved visual/aesthetic appearance.

The discrete particles herein can be in any shape, for example, spherical shape, rectangular shape, diamond shape, planar (flake-shaped) or fiber-shaped (e.g., an elongated particle with an aspect ratio of great than 3:1).

Before adding to the non-aqueous base, the discrete particle is 100% of the mixture composition, i.e., consists of the mixture composition and is solid. However, the particle is not an emulsion and is not coated or encapsulated by, for example, polymers. The surfactants and high melting point fatty compound(s) are present in the discrete particle, with or without other ingredients, at a level, by weight of the discrete particle, of 10% to 100% (e.g., 20% to about 99%, 40% to 95%, 60% to 90%, or even 80% to 85%), in view of having discrete particles of the mixture composition in the non-aqueous base composition and in the product composition.

The discrete particles herein are different from swellable silicone elastomer and swellable thickening polymers and can be free or substantially free of such swellable silicone elastomer and swellable thickening polymer. In the present invention, "the discrete particle and the mixture composition being substantially free of swellable silicone elastomer and swellable thickening polymer" means that: the discrete particle and the mixture composition are free of swellable silicone elastomer and swellable thickening polymer; or, if the discrete particle and the mixture composition contains swellable silicone elastomer and swellable thickening polymer, the level of such swellable silicone elastomer and swellable thickening polymer is very low.

Second Discrete Particle

The product composition of the present invention may comprise a second discrete particle, in addition to the above discrete particle of the present invention which comprises the mixture comprising the surfactant, high melting point fatty alcohol, and benefit agent. The second discrete particle useful herein comprises the mixture excluding the benefit agent, i.e., a mixture comprising a surfactant and a high melting point fatty compound. The components and the properties of the second discrete particles are the same as those described for the above discrete particle of the present invention, except for the inclusion of benefit agents.

Cationic Surfactant

The mixture composition and/or base composition may include a cationic surfactant. Some non-limiting examples of a cationic surfactant include mono-long alkyl quaternized ammonium salt, a combination of mono-long alkyl quaternized ammonium salt and di-long alkyl quaternized ammonium salt, mono-long alkyl amine, and a combination of mono-long alkyl amine and di-long alkyl quaternized ammonium salt.

Long Alkyl Quaternized Ammonium Salt

The cationic surfactant may be a mono- or di-long alkyl quaternized ammonium salts having one or two, respectively, long alkyl chain(s) which has from 12 to 30 carbon atoms (e.g., 16 to 24 carbon atoms or 18 to 22 carbon atoms). The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. An exemplary chemical structure for a long alkyl quaternized ammonium salt is described in U.S. Pat. No. 11,633,338. When used, a di-long alkyl quaternized ammonium salt may be combined with a mono-long alkyl quaternized ammonium salts or mono-long alkyl amine salt, at the weight ratio of 1:1 to 1:5 (e.g., 1:1.2 to 1:5 or 1:1.5 to 1:4), in view of stability in rheology and conditioning benefits.

Some nonlimiting examples of mono-long alkyl quaternized ammonium salt cationic surfactants that may be suitable for use herein include behenyl trimethyl ammonium salt; stearyl trimethyl ammonium salt; cetyl trimethyl ammonium salt; and hydrogenated tallow alkyl trimethyl ammonium salt. Some nonlimiting examples of di-long alkyl quaternized ammonium salt cationic surfactants that may be suitable for use herein include dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Long Alkyl Amine

The cationic surfactants herein may include a long alkyl amine cationic surfactant having one long alkyl chain of 12 to 30 carbon atoms (e.g., 16 to 24 carbon atoms or 18 to 22 carbon atoms). The long alkyl amines herein also include mono-long alkyl amidoamines. Primary, secondary, and tertiary fatty amines may be useful. Particularly useful are tertiary amido amines having an alkyl group of 12 to 22 carbons. Exemplary tertiary amido amines include: stearamidopropyldimethylamine, stearamidopropyldiethylamine, stearamidoethyldiethylamine, stearamidocthyldimethylamine, palmitamidopropyldimethylamine, palmitamidopropyldiethylamine, palmitamidoethyldicthylamine, palmitamidocthyldimethylamine, behenamidopropyldimethylamine, behenamidopropyldiethylamine, behenamidoethyldiethylamine, behenamidoethyldimethylamine, arachidamidopropyldiethylamine, arachidamidopropyldimethylamine, arachidamidoethyldiethylamine, arachidamidocthyldimethylamine, diethylaminoethylstearamide. Some additional non-limiting examples of amines that may be useful herein are disclosed in U.S. Pat. No. 4,275,055.

These amines may be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid, at a molar ratio of amine to acid of 1:0.3 to 1:2 (e.g., 1:0.4 to about 1:1).

High Melting Point Fatty Compound

The mixture composition and, optionally, the base composition contain a high melting point fatty compound for providing hair conditioning benefits such as hair friction reduction, case of product spreading, and/or case of hair detangling, compared to compositions containing no high melting point fatty compounds and/or compared to compositions containing low melting point fatty compounds instead of high melting point fatty compounds. The high melting point fatty compound can also provide improved product stability (e.g., reduced risk of phase separation), compared to compositions containing no high melting point fatty compounds and/or compared to compositions containing low melting point fatty compounds instead of high melting point fatty compounds.

The high melting point fatty compound useful herein have a melting point of 25 °C or higher (e.g., 40 °C or higher, 45 °C or higher, or even 50 °C or higher), but typically less than 90 °C (e.g., less than 80 °C, 70 °C, or 65 °C), in view of easier manufacturing and easier emulsification. The high melting point fatty compound may be a single compound or as a blend or mixture of two or more fatty compounds. When used as such blend or mixture, the melting point of the blend or mixture of fatty compounds is 25 °C or higher (e.g., 40 °C or higher, 45 °C or higher, or even 50 °C or higher).

Some non-limiting examples of high melting point fatty compounds that may be useful herein include fatty alcohols, fatty acids, fatty alcohol derivatives, fatty acid derivatives, and mixtures thereof. It is to be understood that the exemplified fatty compounds may fall into more than one classification, e.g., some fatty alcohol derivatives can also be classified as fatty acid derivatives. However, a given classification is not intended to be a limitation on that particular compound, but is done so for convenience of classification and nomenclature. Further, it is to be appreciated that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols may be particularly suitable for use in the personal care products herein, especially those having 14 to 30 carbon atoms (e.g., 16 to about 22 carbon atoms). These fatty alcohols can be saturated or unsaturated and can be straight or branched chain alcohols. Some particularly suitable fatty alcohols include, for example, cetyl alcohol (having a melting point of about 56 °C), stearyl alcohol (having a melting point of about 58-59 °C), behenyl alcohol (having a melting point of about 71 °C), and mixtures thereof. In some embodiments, the fatty alcohol is a mixture of cetyl alcohol and stearyl alcohol, wherein the weight ratio of cetyl alcohol to stearyl alcohol is 1:9 to 9:1 (e.g., 1:4 to 4:1 or 1:2.3 to 1.5:1).

Silicone Compound

The non-aqueous base composition may include (or consist of) a silicone compound. The silicone compound may have an weight average particle size of 10 nm to 100 μm (e.g., 0.1 μm to 100 μm, 1 μm to 50 μm) in the non-aqueous base composition. The silicone compounds may be present as a single compound or a blend or mixture of two or more silicone compounds. The silicone compound may have a viscosity of 1,000 mPa-s to 2,000,000 mPa·s at 25 °C, as measured using a glass capillary viscometer according to Dow Corning Corporate Test Method CTM0004, Jul. 20, 1970. Some non-limiting example of silicone fluids that may be suitable for use herein include polyalkyl siloxanes, polyaryl siloxanes, polyalkylaryl siloxanes, polyether siloxane copolymers, amino substituted silicones, quaternized silicones, and mixtures thereof. In some instances, amino substituted silicones and/or quaternized silicones may be preferred.

Some non-limiting examples of polyalkyl siloxanes include polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasilâ and TSF 451 series, and from Dow Corning in their Dow Corning SH200 series. The above polyalkylsiloxanes are available, for example, as a mixture with silicone compounds having a lower viscosity. Such mixtures have a viscosity of 1,000 mPa-s to 100,000 mPa-s (e.g., 5,000 mPa-s to about 50,000 mPa-s). Such mixtures may include (i) a first silicone compound having a viscosity of 100,000 mPa-s to 30,000,000 mPa-s at 25 °C, (e.g., 100,000 mPa-s to 20,000,000 mPa-s); and (ii) a second silicone compound having a viscosity of 5 mPa-s to 10,000 mPa-s at 25 °C (e.g., 5 mPa-s to 5,000 mPa-s. Such mixtures useful herein include, for example, a blend of dimethicone having a viscosity of 18,000,000 mPa-s and dimethicone having a viscosity of 200 mPa-s available from GE Toshiba, and a blend of dimethicone having a viscosity of 18,000,000 mPa-s and cyclopentasiloxane available from GE Toshiba. The silicone compounds useful herein also include a silicone gum, which is a polyorganosiloxane material having a kinematic viscosity at 25 °C of greater than or equal to 1,000,000 centistokes. It is recognized that the silicone gums described herein can also have some overlap with the above-disclosed silicone compounds. This overlap is not intended as a limitation on any of these materials. The silicone gums will typically have a mass molecular weight in excess of about 200,000, generally between 200,000 and 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

In some instances, the silicone compounds may include an amino substituted silicone (aminosilicone) that conforms to the general formula (I):

$$(R_1)_aG_{3-a}—Si—(—OSiG_2)_n-(—OSiG_b(R_1)_{2-b})_m—O—SiG_{3-a}(R_1)_a \quad (I)$$

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: $—N(R_2)CH_2—CH_2—N(R_2)_2$; $—N(R_2)_2$; $—N(R_2)_3A^-$; $—N(R_2)CH_2—CH_2—NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Particularly suitable amino silicones may include those corresponding to formula (I) wherein m=0, a=1, q=3, G=methyl, n is 1500 to 1700 (e.g., about 1600); and L is $—N(CH_3)_2$ or $—NH_2$. Another particularly suitable aminosilicone corresponds to formula (I) wherein m=0, a=1, q=3, G=methyl, n is 400 to 600 (e.g., about 500); and L is $—N(CH_3)_2$ or $—NH_2$. Such highly preferred amino silicones can be called as terminal aminosilicones, as one or both ends of the silicone chain are terminated by nitrogen containing group.

The above aminosilicones, when incorporated into the personal care composition or non-aqueous base, can be mixed with solvent having a lower viscosity. Such solvents include, for example, polar or non-polar, volatile or non-volatile oils. Such oils include, for example, silicone oils, hydrocarbons, and esters, for example, selected from the group consisting of non-polar volatile hydrocarbons, volatile cyclic silicones, non-volatile linear silicones, and mixtures thereof. The non-volatile linear silicones useful herein are those having a viscosity of 1 to 20,000 centistokes, preferably from about 20 to about 10,000 centistokes at 25 °C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

Silicone Polymer Containing Quaternary Groups

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The silicone polymer is present at 0.05% to 15% (e.g., 0.1% to 10%, 0.15% to 5%, or 0.2% to 4%) by weight of the personal care composition.

The polyorganosiloxane compounds can have the general formulas (Ia) and (Ib):

$$M-Y—[—(N^+R_2-T-N^+R_2)—Y-]_m-[—(NR^2-A-E-A'—NR^2)—Y-]_k-M \quad (Ia)$$

$$M-Y—[—(N^+R_2-T-N^+R_2)—Y-]_m-[—(N^+R^2{}_2-A-E-A'-N^+R^2{}_2)—Y-]_k-M \quad (Ib)$$

wherein:

m is >0, 0.01 to 100 (e.g., 0.1 to 100, 1 to 100, 1 to 50, 1 to 20, or 1 to 10), k is 0 or an average value of >0 to 50 (e.g., 1 to 20 or 1 to 10), M represents a terminal group, comprising terminal ester groups selected from

—OC(O)—Z

—$OS(O)_2$—Z

—$OS(O_2)O$—Z

—OP(O)(O—Z)OH

—$OP(O)(O—Z)_2$ wherein Z is selected from monovalent organic residues having up to 40 carbon atoms, optionally comprising one or more hetero atoms.

A and A' each are independently from each other selected from a single bond or a divalent organic group having up to 10 carbon atoms and one or more hetero atoms, and E is a polyalkylene oxide group of the general formula:

$$—[CH_2CH_2O]_q—[CH_2CH(CH_3)O]_r—[CH_2CH(C_2H_5)O]_s—$$

wherein q=0 to 200, r=0 to 200, s=0 to 200, and q+r+s=1 to 600.

$R^2$ is selected from hydrogen or R,

R is selected from monovalent organic groups having up to 22 carbon atoms and optionally one or more heteroatoms, and wherein the free valencies at the nitrogen atoms are bound to carbon atoms, Y is a group of the formula:

—K—S—K—and -A-E-A'-or-A'-E-A-, with S=

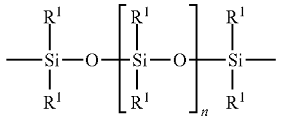

wherein R1=$C_1$-$C_{22}$-alkyl, $C_1$-$C_{22}$-fluoralkyl or aryl; n=200 to 1000, and these can be identical or different if several S Groups are present in the polyorganosiloxane compound.

K is a bivalent or trivalent straight chain, cyclic and/or branched $C_2$-$C_{40}$ hydrocarbon residue which is optionally interrupted by-O—,—NH—, trivalent N, —$NR_1$—, —C(O)—, —C(S)—, and optionally substituted with-OH, wherein $R^1$ is defined as above, T is selected from a divalent organic group having up to 20 carbon atoms and one or more hetero atoms.

The residues K may be identical or different from each other. In the —K—S—K-moiety, the residue K is bound to the silicon atom of the residue S via a C—Si-bond.

Due to the possible presence of amine groups (—($NR^2$-A-E-A'—$NR^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

The molar ratio of the quaternary ammonium groups b) and the terminal ester groups c) may be less than 100:20 (e.g., less than 100:30 or less than 100:50). The ratio can be determined by $^{13}$C-NMR.

The polyorganosiloxane composition may comprise:

A. at least one polyorganosiloxane compound, comprising a) at least one polyorganosiloxane group, b) at least one quaternary ammonium group, c) at least one terminal ester group, and d) at least one polyalkylene oxide group (as defined before), B. at least one polyorganosiloxane compound, comprising at least one terminal ester group, different from compound A.

In the definition of component A) it can be referred to the description of the polyorganosiloxane compounds herein. The polyorganosiloxane compound B) can differ from the polyorganosiloxane compound A) in that it does not comprise quaternary ammonium groups. Polyorganosiloxane compounds B) result from the reaction of monofunctional organic acids, in particular carboxylic acids, and polyorganosiloxane containing bisepoxides.

When present in the personal care composition, the weight ratio of compound A) to compound B) may be less than 90:10 (i.e., component B) is present at at least 10 weight percent). The polyorganosiloxane compositions in compound A) may have a molar ratio of the quaternary ammonium groups b) and the terminal ester groups c) of less than 100:10 (e.g., less than 100:15 and less than 100:20).

The silicone polymer has a viscosity at 20 °C and a shear rate of $0.1s^{-1}$ (plate-plate system, plate diameter 40 mm, gap width 0.5 mm) of less than 100,000 mPas (100 Pas). In further embodiments, the viscosities of the neat silicone polymers may range from 500 to 100,000 mPas, (e.g., 500 to 70,000 mPas, 500 to 50,000 mPas, or 500 to 20,000 mPas). The viscosities of the neat polymers may range from 500 to 10,000 mPas (e.g., 500 to 5000 mPas) determined at 20 °C and a shear rate of 0.1 $s^{-1}$.

In the polyalkylene oxide group E of the general formula:

$$—[CH_2CH_2O]_q—[CH_2CH(CH_3)O]_r,[CH_2CH(C_2H_5)O]_s—$$

the q, r, and s indices may be defined as follows:

q=0 to 200 (e.g., 0 to 100, 0 to 50, or even 0 to 20), r=0 to 200 (e.g., 0 to 100, 0 to 50, or even 0 to 20), s=0 to 200 (e.g., 0 to 100, 0 to 50, or even 0 to 20), and q+r+s=1 to 600 (e.g., 1 to 100, 1 to 50, or even 1 to 40).

For polyorganosiloxane structural units with the general formula S:

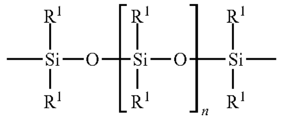

$R^1$=$C_1$-$C_{22}$-alkyl, $C_1$-$C_{22}$-fluoralkyl and aryl; n=from 200 to 1000 (e.g., 300 to 500), K (in the group —K—S—K—) is a bivalent or trivalent straight chain, cyclical or branched $C_2$-$C_{20}$ hydrocarbon residue which is optionally interrupted by —O—, —NH—, trivalent N, —$NR^1$—, —C(O)—, —C(S)—, and optionally substituted with —OH.

In some instance, $R^1$ is $C_1$-$C_{18}$ alkyl, $C_1$-$C_{18}$ fluoroalkyl and aryl (e.g., $C_1$-$C_{18}$ alkyl, $C_1$-$C_6$ fluoroalkyl and aryl). In other instances, $R^1$ is $C_1$-$C_6$ alkyl and $C_1$-$C_6$ fluoroalkyl. In still other instances $R^1$ is $C_1$-$C_4$ fluoroalkyl and phenyl. It may be particularly desirable for $R^1$ to be methyl, ethyl, trifluoropropyl and phenyl.

As used herein, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term “aryl” means unsubstituted or phenyl substituted once or several times with OH, F, Cl, $CF_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Additional Components

The non-aqueous base composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of 0.001% to 10%.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithionc.

Method of Preparation of Product Compositions

The product composition of the present invention can be prepared by, for example, below METHOD A or METHOD B.

Method A

Prepare a mixture composition comprising a surfactant and a high melting point fatty compound and a benefit agent, for example, as described in more detail below. Separately prepare a non-aqueous base composition comprising at least 75% of a fluid that is not a hydrogen donor, for example, as described below. Mix the mixture composition and the non-aqueous base composition, to form a discrete particle of the mixture composition dispersed in the non-aqueous base composition. When mixed, the mixture composition and the non-aqueous base composition respectively have a temperature lower than the melting point of the high melting point fatty compound. When mixed, the mixture composition has a temperature lower than the melting point of the high melting point fatty compound contained in the mixture composition, and the mixture composition has such temperature during and after mixing with the non-aqueous base composition. The non-aqueous base composition also has a temperature lower than the melting point of the high melting point fatty compound contained in the mixture composition when mixed with the mixture composition and has such temperature during and after mixing with the mixture composition. Thus, when mixed, the mixture composition and the non-aqueous base composition respectively have a temperature of at least 2 °C lower (e.g., 5 °C lower, 10 °C lower, or 15 °C lower) than the melting point of the high melting point fatty compound. When mixed, the mixture composition and the non-aqueous base composition respectively have a temperature of from about 0 °C to about 50 °C (e.g., 10 °C to 40 °C or 15 °C to 35 °C).

Method B

Prepare a mixture composition comprising a surfactant and a high melting point fatty compound and a benefit agent, for example, as described in more detail below. Separately prepare a non-aqueous base composition comprising at least 75% of a fluid that is not a hydrogen donor, for example, as described below. Mix the discrete particle and the non-aqueous base composition, to disperse the discrete particle in the non-aqueous base composition. The discrete particle may be solid. A solvent or carrier may be used to prepare discrete particle of the mixture composition. Such solvents and carriers are considered as components of the non-aqueous base composition when determining amounts of ingredients. When mixed, the discrete particle and the non-aqueous base composition respectively have a temperature lower than the melting point of the high melting point fatty compound. When mixed, the discrete particle has a temperature lower than the melting point of the high melting point fatty compound contained in the discrete particle, and the discrete particle has such temperature during and after mixing with the non-aqueous base composition. Also preferably, the non-aqueous base composition also has a temperature lower than the melting point of the high melting point fatty compound contained in the discrete particle when mixed with the discrete particle, and has such temperature during and after mixing with the discrete particle. When mixed, the discrete particle and the non-aqueous base composition respectively have a temperature of preferably at least 2 °C lower (e.g., 5 °C lower, 10 °C lower, or 15 °C lower) than the melting point of the high melting point fatty compound. When mixed, the discrete particle and the non-aqueous base composition respectively have a temperature of 0 °C to 50 °C (e.g., 10 °C to 40 °C or 15 °C to 35 °C)

Preparation of the Mixture Composition

Both in METHOD A and B, the mixture composition is prepared by preparing a mixture composition comprising the surfactant and the high melting point fatty compound, wherein the temperature of the mixture composition is higher than the melting point of the high melting point fatty compound contained in the mixture composition, and then cooling the mixture composition to a temperature which is lower than the melting point of the high melting point fatty compound. In METHOD B, the discrete particle can be prepared concurrently when preparing the mixture composition during the above cooling step, or can be prepared after forming the mixture composition.

The temperature of the melted mixture composition is at least 2 °C (e.g., 5 °C, 10 °C, or 15 °C) higher than the above melting point of the high melting point fatty compound. The temperature of the melting mixture composition can be 30 °C to 150 °C (e.g., 40 °C to 100 °C, 50 °C to 95 °C, 55 °C to 90 °C, or 66 °C to 90 °C). The molten mixture composition is cooled to a temperature which is lower than a melting point of the high melting point fatty compound contained in the mixture composition, i.e., at least 2 °C lower than the melting point of the high melting point fatty compound contained in the mixture composition. In some instances, the mixture composition may be cooled to a temperature of −200 °C to about 50 °C (e.g., −40 °C to 50 °C or 0 °C to about 30 °C).

When Containing the Benefit Agents in the Mixture Composition

When the mixture composition further comprises the benefit agents, the mixture composition can be prepared by steps of:

Preparing a melting mixture composition comprising the surfactant and the high melting point fatty compound, wherein the temperature of the melting mixture composition is higher than a melting point of the high melting point fatty compound contained in the mixture composition;

Cooling the melting mixture composition to the temperature which is lower than a melting point of the high melting point fatty compound contained in the mixture composition, to form the mixture composition, wherein the benefit agent can be added anytime depending on the properties of the benefit agent, for example, the benefit agent can be added to the mixture composition before cooling, during cooling especially when using volatile benefit agent such as perfumes, or after cooling preferably right after cooling such as within 30 min after cooling.

When the mixture composition comprises a benefit agent, the benefit agent can be homogeneously mixed with the mixture composition, and homogeneous discrete particles can be formed in the compositions.

Alternatively, in the discrete particle, the benefit agent can form an inner core covered by an outer shell formed by the mixture composition.

When Containing the Benefit Agent in the Non-Aqueous Base Composition

When the non-aqueous base composition comprises a benefit agent, the benefit agent can be homogeneously mixed with the non-aqueous base composition.

When the non-aqueous base composition comprises a benefit agent, the benefit agent can be added to the non-aqueous base composition anytime, for example, before adding the mixture composition and/or the discrete particle, after adding the mixture composition and/or the discrete particle, and/or concurrently with the discrete particle.

Test Methods

4 Week Stability Test:

This is a Test Method for Stability, that is, for determining failure/success due to disintegration.

0.2 g of the discrete particles are added to 99.8 g of the non-aqueous base and placed in a temperature-controlled room, at 40 degrees Celsius. The appearance of the non-aqueous base and discrete particles is checked after 4 weeks. The mixture should be placed in a see-through container to aid the assessment.

FIG. 1 is an example of the initial appearance of a sample that has been successfully formulated, i.e., forms discrete particles within the non-aqueous base. FIG. 1 is an initial photo (i.e., right after making the example) of inventive example 3, however it is a good representation of any of the initial example appearances, both inventive and comparative.

FIG. 2 is an example of an inventive composition, as it has stable discrete particles after 4 weeks under the 4 Week Stability Test. After four weeks, the discrete particles remain discrete particles with no disintegration. To be considered stable, all particles should remain discrete and intact. The particles may change in their absolute size or volume but should still remain discrete. FIG. 2 is a photo of Inventive Example 5 after 4 weeks under the 4 Week Stability Test.

FIG. 3 shows an example of disintegration of discrete particles after 4 weeks under the 4 Week Stability Test. This comparative example, while initially formulated with discrete particles, did not remain stable and the discrete particles disintegrated and/or dissolved. FIG. 3 is a photo of Comparative Example 1, taken after 4 weeks under the 4 Week Stability Test.

For non-inventive or comparative examples, the presence of a hydrogen donor within the non-aqueous base composition leads to higher polarity and thus higher interaction and compatibility between the discrete particle and the non-aqueous base composition. The higher compatibility and interaction eventually lead to disintegration or dissolving of the non-aqueous composition in a “like dissolves like” concept. Thus, stability is achieved when the non-aqueous base comprises at least about 75% of a non-hydrogen donor fluid.

ALogP:

ALogP is the Octanol/Water partition coefficient that describes the hydrophilicity or hydrophobicity of the molecule. “AlogP” as used herein, is an identification of the octanol-water partition coefficient of an active. Ghose and Crippen used this atom-based method to calculate the octanol-water partition coefficient (log P), and the molar refractivity (MR) for incoming molecules. Log P provides a measure of the hydrophobicity of the molecule, while MR contains information about molecular volume and polarizability. AlogP is calculated herein using Pipeline Pilot software (Biovia™) ver 9.2.

Method of Preparation of the Product Composition

The embodiments disclosed and represented in Table 3 are hair conditioning product compositions of the present invention, and were prepared by Method B explained above, and the following in more detail:

Preparing the mixture composition comprising the surfactant and the high melting point fatty compound and benefit agent, wherein the mixture composition was prepared by the following method:

Preparing a melting mixture composition wherein the temperature of the melting mixture composition is higher than a melting point of the high melting point fatty compound contained in the mixture composition, i.e., from about 66 °C to about 90 °C;

Cooling the melting mixture composition to a temperature which is lower than a melting point of the high melting point fatty compound contained in the mixture composition, i.e., from about 0 °C to about 40 °C, to form the mixture composition;

Preparing a solid discrete particle consisting of the mixture composition;

Separately preparing a non-aqueous base composition;

Mixing the discrete particle and the non-aqueous base composition, both having a temperature lower than a melting point of the high melting point fatty compound contained in the mixture composition, i.e., from about 10 °C to about 40 °C, so that the discrete particle is dispersed in the non-aqueous base composition.

The hair conditioner product compositions disclosed in Table 4 are comparative examples and were prepared by the above METHOD B.

Examples

Table 1 below shows various materials and their ALogP and number of hydrogen donors. As can be seen in Tables 1-4, when a material has satisfied both conditions of not being a hydrogen donor and having an AlogP of at least 6, the non-aqueous product composition is able to maintain the solid discrete particles for at least 4 weeks at 40 °C. For clarity, a fluid that does not comprise any hydrogen donor groups is a fluid that is not a hydrogen donor.

TABLE 1

Materials and their ALogP and Number of Hydrogen Donors

| | AlogP | H Donor | Has both 0 H donation and AlogP of at least 6 | Solid Discrete particles visible after 4 weeks 40° C. |
|---|---|---|---|---|
| 1-Decanol | 3.71 | 1 | NO | NO |
| Hexyldecanol | 6.43 | 1 | NO | NO |
| Oleic acid | 6.86 | 1 | NO | NO |
| Oleyl Alcohol | 6.91 | 1 | NO | NO |
| 1-Octanol | 2.80 | 1 | NO | NO |
| Isohexadecane | 7.47 | 0 | YES | YES |
| Isododecane | 6.95 | 0 | YES | YES |
| Triethylhexanoin | 8.59 | 0 | YES | YES |
| Isodecyl Oleate | 11.15 | 0 | YES | YES |
| Decyl oleate | 10.95 | 0 | YES | YES |
| Silicone Quaternium-26 | n/a | 0 | YES | YES |
| Cyclopentasiloxane | n/a | 0 | YES | YES |
| Dimethicone | n/a | 0 | YES | YES |

Tables 2-4 show the compositions (non-aqueous base and mixture composition (discrete particles)) that populate Table 1.

TABLE 2

Composition of solid discrete particles

| | A1 | B1 | C1 | D1 |
|---|---|---|---|---|
| Cetyl Alcohol | 45 | 45 | 45 | 30 |
| Stearyl Alcohol | 45 | 45 | 45 | 30 |
| BTMS | 5 | | | 35 |
| SAPDMA | | 5 | | |
| BTMAC | | | 10 | |
| Benefit Agent | 5 | 5 | | 5 |

TABLE 3

Inventive Examples of Conditioner Product Compositions

| | Inv 1 | Inv 1 | Inv 3 | Inv 4 | Inv 5 | Inv 6 | Inv 7 | Inv 8 | Inv 9 |
|---|---|---|---|---|---|---|---|---|---|
| A1 | 0.2 | 0.2 | 0.2 | 0.2 | 0.2 | | | 0.2 | 0.2 |
| B1 | | | | | | 0.2 | | | |
| C1 | | | | | | | 0.2 | | |
| 1-Decanol | | | | | | | | 24.8 | |
| Isohexadecane | | 99.8 | | | | | | | |
| Isododecane | | | | | | | | | 60 |
| Triethylhexanoin | 99.8 | | | | | 99.8 | 99.8 | 75 | |
| Isodecyl Oleate | | | 99.8 | | | | | | |
| Decyl oleate | | | | 99.8 | | | | | |
| Silicone Quaternium-26 | | | | | 99.8 | | | | |

TABLE 3-continued

| Inventive Examples of Conditioner Product Compositions | | | | | | | | | |
|---|---|---|---|---|---|---|---|---|---|
| | Inv 1 | Inv 1 | Inv 3 | Inv 4 | Inv 5 | Inv 6 | Inv 7 | Inv 8 | Inv 9 |
| Dimethicone | | | | | | | | | 30 |
| Other materials | | | | | | | | | 9.8 |
| No Hydrogen Donor (>75% of composition)? | Yes | Yes | Yes | Yes | Yes | Yes | Yes | Yes | Yes |
| Does not dissolve at 4 weeks 40 °C | Yes | Yes | Yes | Yes | Yes | Yes | Yes | Yes | Yes |

TABLE 4

| Conditioner product compositions for Table 1: Comparative Examples | | | | | | | | | |
|---|---|---|---|---|---|---|---|---|---|
| | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
| A1 | 0.2 | 0.2 | 0.2 | 0.2 | 0.2 | | | 0.2 | 0.2 |
| B1 | | | | | | 0.2 | | | |
| C1 | | | | | | | 0.2 | | |
| 1-Decanol | 99.8 | | | | | 99.8 | 99.8 | 50 | 75 |
| Hexyldecanol | | 99.8 | | | | | | | |
| Oleic acid | | | 99.8 | | | | | | |
| Oleyl Alcohol | | | | 99.8 | | | | | |
| Triethylhexanoin | | | | | | | | 49.8 | 24.8 |
| 1-Octanol | | | | | 99.8 | | | | |
| No Hydrogen Donor (>75% of composition)? | No | No | No | No | No | No | No | No | No |
| Does not dissolve at 4 weeks 40 C | No | No | No | No | No | No | No | No | No |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm.”

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:

discrete particles of a mixture composition, wherein the mixture composition comprises a surfactant and a high melting point fatty compound; and a non-aqueous base, wherein the non-aqueous base comprises at least 75 wt. % of a fluid that is not a hydrogen donor.

2. The personal care composition of claim 1, wherein the fluid has an AlogP of at least 6.

3. The personal care composition of claim 1, wherein the non-aqueous base comprises at least 90%, by weight of the base, of the fluid.

4. The personal care composition of claim 1, wherein the fluid comprises at least one of a silicone, a branched hydrocarbon, an ester, and an alkane.

5. The personal care composition of claim 4, wherein the fluid is a silicone selected from a polyalkylsiloxane, a cyclopentasiloxane, a dimethicone, an aminosilicone, and combinations thereof.

6. The personal care composition of claim 1, wherein the fluid comprises at least one of isohexadecane, isododecane, triethylhexanoin, isodecyl oleate, decyl oleate, silicone quaternium-26, dimethicone, and cyclopentasiloxane.

7. The personal care composition of claim 1, wherein the fluid has a melt point below 25 °C.

8. The personal care composition of claim 1, wherein the composition is free of or substantially free of anionic surfactants, zwitterionic surfactant, and amphoteric surfactants.

9. The personal care composition of claim 1, wherein the discrete particles are not coated or encapsulated.

10. The personal care composition of claim 1, wherein the discrete particles are stable according to the 4 Week Stability Test.

11. The personal care composition of claim 1, wherein the discrete particles comprise less than about 30% of water.

12. The personal care composition of claim 11, wherein the discrete particle is anhydrous.

13. The personal care composition of claim 1, wherein the surfactant is a cationic surfactant, a nonionic surfactant, or a mixture thereof.

14. The personal care composition of claim 13, wherein the surfactant is a cationic surfactant.

15. The personal care composition of claim 1, wherein the personal care composition is a hair oil composition.

16. The personal care composition of claim 1, wherein the discrete particles further comprise a benefit agent.

17. The personal care composition of claim 16, wherein the benefit agent comprises a silicone compound, a perfume, an incompatible agent, or a combination thereof.

18. The personal care composition of claim 1, wherein the non-aqueous base comprises 100%, by weight of the base, of the fluid that is not a hydrogen donor.

* * * * *